US009074226B2

(12) United States Patent
Takebayashi et al.

(10) Patent No.: US 9,074,226 B2
(45) Date of Patent: Jul. 7, 2015

(54) ISOPROPYL ALCOHOL-PRODUCING BACTERIUM AND METHOD OF PRODUCING ISOPROPYL ALCOHOL USING THE SAME

(75) Inventors: Nozomi Takebayashi, Mobara (JP); Mitsufumi Wada, Chiba (JP); Daisuke Mochizuki, Mobara (JP); Fuminobu Yoshimi, Mobara (JP); Seiichi Watanabe, Mobara (JP); Hitoshi Takahashi, Chiba (JP); Takashi Morishige, Mobara (JP)

(73) Assignee: MITSUI CHEMICALS, INC., Tokyo (JP)

( * ) Notice: Subject to any disclaimer, the term of this patent is extended or adjusted under 35 U.S.C. 154(b) by 412 days.

(21) Appl. No.: 12/452,564

(22) PCT Filed: Jul. 4, 2008

(86) PCT No.: PCT/JP2008/062205
§ 371 (c)(1),
(2), (4) Date: Jan. 8, 2010

(87) PCT Pub. No.: WO2009/008377
PCT Pub. Date: Jan. 15, 2009

(65) Prior Publication Data
US 2010/0311135 A1 Dec. 9, 2010

(30) Foreign Application Priority Data
Jul. 11, 2007 (JP) ................................. 2007-181571

(51) Int. Cl.
C12N 1/20 (2006.01)
C12P 7/04 (2006.01)
C12P 7/02 (2006.01)
C12P 7/28 (2006.01)
C07H 21/04 (2006.01)
C12N 9/04 (2006.01)
C12N 9/10 (2006.01)
C12N 9/88 (2006.01)
C12M 1/00 (2006.01)

(52) U.S. Cl.
CPC ................. *C12P 7/04* (2013.01); *C12N 9/0006* (2013.01); *C12N 9/1029* (2013.01); *C12N 9/13* (2013.01); *C12N 9/88* (2013.01); *C12M 21/12* (2013.01); *C12M 47/10* (2013.01); *C12M 47/20* (2013.01)

(58) Field of Classification Search
CPC ........ C12P 7/04; C12P 7/065; C12P 2203/00; C12P 5/02; Y02E 50/10; Y02E 50/343; Y02E 50/30; C12N 9/0006; C12N 9/1029; C12N 1/20; C12N 9/0004; C12N 15/74; C12N 9/0036; C12N 9/54; C07K 14/245; C07K 14/33; C12R 1/145; C12R 1/07; C12Y 401/01004; C12Y 203/01009; C12Y 101/0108; C12Y 301/02
See application file for complete search history.

(56) References Cited

U.S. PATENT DOCUMENTS

2008/0182308 A1* 7/2008 Donaldson et al. ........... 435/160
2010/0221800 A1* 9/2010 Liao et al. ..................... 435/157

FOREIGN PATENT DOCUMENTS

| CN | 1043956 A | 7/1990 |
|---|---|---|
| JP | 56-1886 | 1/1981 |
| JP | 61-67493 | 4/1986 |
| WO | WO 2007/041269 A2 | 4/2007 |
| WO | WO 2008/131286 A1 | 10/2008 |
| WO | WO-2009/078973 A2 | 6/2009 |

OTHER PUBLICATIONS

Fontaine et al. Molecular characterization and transcriptional analysis of adhE2, the gene encoding the NADH-dependent aldehyde/alcohol dehydrogenase responsible for butanol production in alcohologenic cultures of *Clostridium acetobutylicum* ATCC 824, J Bacteriol. 2002, 184(3): 821-830.*

Bermejo, Lourdes L. et al., "Expression of *Clostridium acetobutylicum* ATCC 824 Genes in *Escherichia coli* for Acetone Production and Acetate Detoxification," Applied and Environmental Microbiology, Mar. 1998, vol. 64, No. 3, pp. 1079-1085.

Dominguez, Jose M. et al., "Ethanol Pruduction from Xylose with the Yeast *Pichia stipitis* and Simultaneous Product Recovery by Gas Stripping Using a Gas-Lift Loop Fermentor with Attached Side-Arm (GLSA)," Biotechnology and Bioengineering, Feb. 5, 2000, vol. 67, No. 3, pp. 336-343.

Yan, Run-Tao et al., "Expression of Solvent-Forming Enzymes and Onset of Solvent Production in Batch Cultures of *Clostridium beijerinckii* ("*Clostridium butylicum*")," Applied and Environmental Microbiology, Mar. 1988, vol. 54, No. 3, pp. 642-648.

Imanaka, Tadayuki, Biseibutsu Riyo No Daitenkai, NTS Inc., Jul. 25, 2002, Kuchie 43, 2 pgs.

Fischer, R. J. et al., Database GenBank [online], Accession No. X72831, http://ww.ncbi.nlm.nih.gov/entrez/viewer.fcgi?db=nuccore&id=298080, uploaded Jun. 12, 2006, retrieved on Aug. 6, 2008, Definition: *C.acetobutylicum* adhE, ctfA and crfB genes, 6 pgs.

Gerischer, U. et al., Database GenBank [online], Accession No. M55392, http://www.ncbi.nlm.nih.gov/entrez/viewer.fcgi?db=nuccore&id=6466901, uploaded Nov. 24, 1999, retrieved on Aug. 6, 2008, Definition: *Clostridium acetobutylicum* alpha-amylase AmyA precursor (amyA) and acetoacetate decarboxylase (adc) genes, complete cds; and unknown genes, 4 pgs.

(Continued)

*Primary Examiner* — Iqbal H Chowdhury

(74) *Attorney, Agent, or Firm* — Foley & Lardner LLP

(57) ABSTRACT

The invention provides: an isopropyl alcohol-producing bacterium which has an acetoacetate decarboxylase activity, an isopropyl alcohol dehydrogenase activity, a CoA transferase activity and a thiolase activity having been imparted thereto and is capable of producing isopropyl alcohol from a plant-derived material; a method of producing isopropyl alcohol whereby isopropyl alcohol is produced from a plant-derived material by using this isopropyl alcohol-producing bacterium; and an apparatus therefor.

18 Claims, 1 Drawing Sheet

(56) References Cited

OTHER PUBLICATIONS

Toth, J. et al., Database GenBank [online], Accession No. AF157307, http://www.ncbi.nlm.nih.gov/entrez/viewer.fcgi?db=nuccore &id=60592972, uploaded Mar. 9, 2005, retrieved on Aug. 6, 2008, Definition: *Clostridium beijerinckii* strain NRRL B593 putative transcription activator (stc), NAPD-dependent alcohol dehydrogenase (adh), and putative electron-transfer protein (hydG) genes, complete cds; and putative glutamate synthase small subunit (gltD) gene, partial cds., 4 pgs.

Nolling, J. et al., Database GenBank [online], Accession No. AE001437, http://www.ncbi.nlm.nih.gov/entrez/viewer.fcgi?db=nuccore&id=25168256, uploaded Jan. 19, 2006, retrieved on Aug. 6, 2008, Definition: *Clostridium acetobutylicum* ATCC 824, complete genome, 1 pg.

Blattner, F. R. et al., Database GenBank [online], Accession NO. U00096, http://www.ncbi.nlm.nih.gov/entrez/viewer.fcgi?48994873:NCBI:175260, uploaded Apr. 24, 2007, retrieved on Aug. 6, 2008, Definition: *Escherichia coli* K12 MG1655, complete genome, 1 pg.

Hanai, T. et al., "Engineered Synthetic Pathway for Isopropanol Production in *Escherichia coli*," Applied and Environmental Microbiology, Dec. 2007, vol. 73, No. 24, pp. 7814-7818.

Jojima, Toru et al., "Production of Isopropanol by Metabolically Engineered *Escherichia coli*," Applied and Microbiology Biotechnology, Jan. 2008, vol. 77, No. 6, pp. 1219-1224.

Communication (Supplementary EP Search Report) in EP Appln No. 08 79 0886 dated May 13, 2011.

Third Notice of Opinion on Examination Chinese Patent Application No. 200880023907.2 dated Mar. 21, 2013.

\* cited by examiner

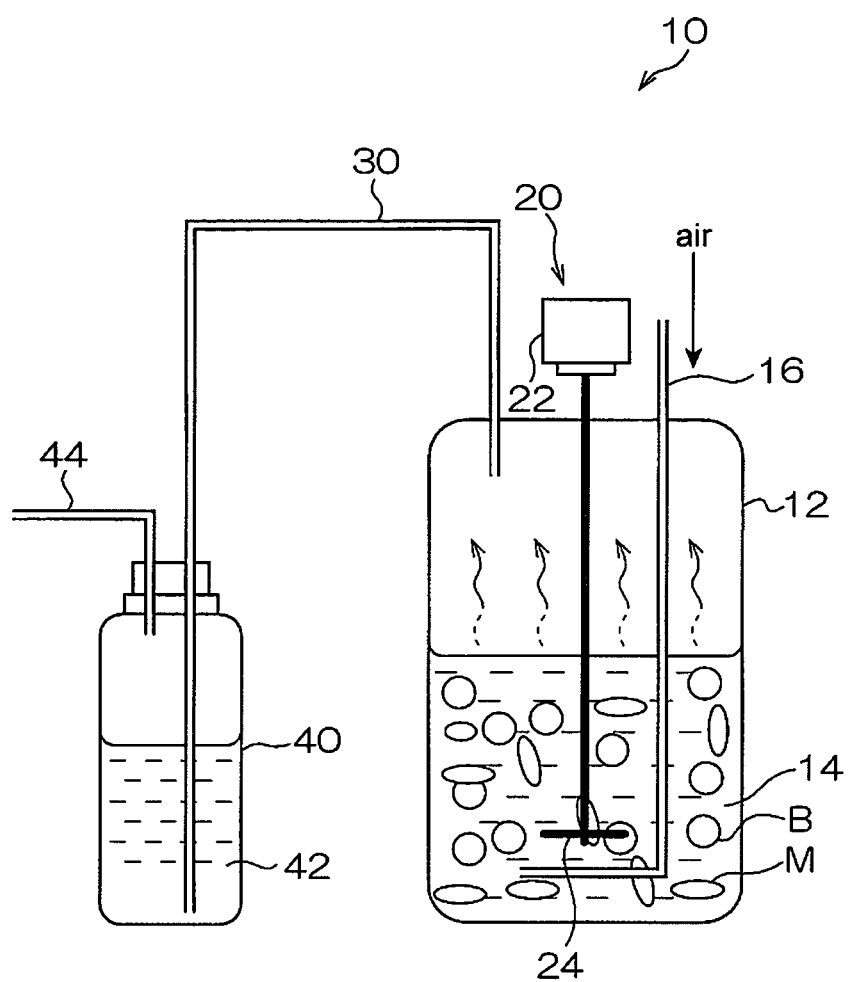

SEQUENCE LISTING

<160> NUMBER OF SEQ ID NOS: 28

<210> SEQ ID NO 1
<211> LENGTH: 37
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
tttgaattcc atgattttaa gggggttagc atatgca        37

<210> SEQ ID NO 2
<211> LENGTH: 39
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 2
tttggtaccc tagcactttt ctagcaatat tgctgttcc                                    39

<210> SEQ ID NO 3
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tttggtaccc aaccttaaac cttcatattt caactactt                                    39

<210> SEQ ID NO 4
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tttggatccc taaacagcca tgggtctaag ttc                                          33

<210> SEQ ID NO 5
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tttggatcca gctaaacatt attaaattta ggaaggtg                                     38

<210> SEQ ID NO 6
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tttgtcgacc caatgaactt agacccatgg ctg                                          33

<210> SEQ ID NO 7
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tttggtaccg cgaaatagcg atgaacaggc ag                                           32

<210> SEQ ID NO 8
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 8
tttggtaccg cagattttgc tactcttgga gc                                   32

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cgagctacat atgcaatgat tgacacgatt ccg                                  33

<210> SEQ ID NO 10
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cgcgcgcatg ctatttgtta gtgaataaaa gg                                   32

<210> SEQ ID NO 11
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
aatatgcatg ctggtggaac atatgaaagg ttttgcaatg ctagg                     45

<210> SEQ ID NO 12
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gcggatccgg taccttataa tataactact gctttaatta agtc                      44

<210> SEQ ID NO 13
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
atggatccgc tggtggaaca tatgaaaaat tgtgtcatcg tcag                      44

<210> SEQ ID NO 14
<211> LENGTH: 42
<212> TYPE: DNA
<213> ORGANISM: Artificial Sequence
<220> FEATURE:
<223> OTHER INFORMATION: Description of Artificial Sequence: Synthetic
      primer -continued

<400> SEQUENCE: 14
gcagaagctt gtctagatta attcaaccgt tcaatcacca tc                          42

<210> SEQ ID NO 15
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gctctagagc tggtggaaca tatgaaaaca aaattgatga cattacaaga c                51

<210> SEQ ID NO 16
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tagcaagctt ctactcgagt tatttgctct cctgtgaaac g                           41

<210> SEQ ID NO 17
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
aagtctcgag ctggtggaac atatggatgc gaaacaacgt attg                        44

<210> SEQ ID NO 18
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ggccaagctt cataaatcac cccgttgc                                          28

<210> SEQ ID NO 19
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
caggtaccgc tggtggaaca tatgttaaag gatgaagtaa ttaaacaaat tagc             54

<210> SEQ ID NO 20
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gcggatcctt acttaagata atcatatata acttcagc        38

<210> SEQ ID NO 21
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tttgaattcc atgattttaa ggggttagc atatgca          37

<210> SEQ ID NO 22
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ttttctagat ctaactaacc tcctaaattt tgatacggg       39

<210> SEQ ID NO 23
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
tttctcgagg cagattttgc tactcttgga gc              32

<210> SEQ ID NO 24
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tttggtaccg cagattttgc tactcttgga gc              32

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
tcgaccggct ccagttcg                              18

<210> SEQ ID NO 26
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26

```
ctgtcgcatg ctgactcagc taacaataaa atttttgg                              38

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
cgactcgcat atgtcgtttt tctgcttagg                                       30

<210> SEQ ID NO 28
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
cagtcgcatg cttcgaactc cttaaattta tttgaaggc                             39
```

ISOPROPYL ALCOHOL-PRODUCING BACTERIUM AND METHOD OF PRODUCING ISOPROPYL ALCOHOL USING THE SAME

TECHNICAL FIELD

The present invention relates to an isopropyl alcohol-producing bacterium and a method of producing isopropyl alcohol using the same.

BACKGROUND ART

Isopropyl alcohol produced from a plant-derived material can be converted to propylene through dehydration, so that it is promising as a carbon-neutral raw material for propylene. Since all the developed countries are currently required by Kyoto Protocol to reduce their amounts of carbon dioxide emissions by 5% based on those in 1990, carbon-neutral propylene is extremely important due to its versatility in view of the global environment.

Bacteria that utilize plant-derived materials to produce isopropyl alcohol (e.g., see Chinese Patent Application Publication No. CN 1043956 A and Japanese Patent Application laid-Open (JP-A) No. 61-67493) already exist in nature. However, they are known to have low productivity of isopropyl alcohol and to generate alcohols such as butanol and ethanol as by-products. Since the azeotropic temperatures of butanol and ethanol are close to that of water, it is difficult to separate isopropyl alcohol from butanol and/or ethanol by easy methods such as simple distillation. Therefore, it is thought that collection of isopropyl alcohol from fermentation broth in which butanol and/or ethanol coexist(s) with isopropyl alcohol requires distillation using incidental facilities such as a rectifying column, so that the purification process is expected to be complicated.

CN 1043956 A describes a method for producing butanol, ethanol, acetone and isopropanol in which *Clostridium Butanoiacetonicus* G.V is cultured in a culture medium, which has been supplemented with maize and molasses, and subjecting the thus-obtained culture to distillation redistillation and fractional distillation. However, in Examples described in the literature, yields of butanol, ethanol, acetone and isopropanol in the culture medium are not described at all, and the amount of each of these components which should have been finally obtained by the fractional distillation is not described. Thus, the actual production of isopropanol, butanol, ethanol and acetone cannot be seen from the literature.

JP-A 61-67493 describes that the culture medium obtained by culturing a bacterium of the genus *Clostridium* contains butanol, the amount of which is larger than that of isopropyl alcohol, and small amounts of ethanol and acetone. This literature describes that a common method of separation and purification to obtain isopropyl alcohol from the obtained culture medium is a method in which the culture medium is filtered, distilled several times, concentrated and subjected to separation by salting out to obtain an oil content, which is subsequently subjected to fractional distillation by an apparatus having a fractionating column.

On the other hand, it has been known that acetone can be produced by introducing, to *E. coli*, genes of acetoacetate decarboxylase, CoA transferase and thiolase which are derived from a bacterium of the genus *Clostridium* (*Clostridium Acetobutylicum*) and culturing the obtained recombinant *E. coli* (e.g., Lourdes L Bermejo et al.: Applied and Environmental Microbiology, Vol. 64, N0.3, p. 1079-1085, (1998)).

DISCLOSURE OF THE INVENTION

Problems to be Solved by the Invention

As described above, the existing isopropyl alcohol-producing bacteria have low productivity of isopropyl alcohol and, in addition, produce a large amount of alcohols such as butanol and ethanol as by-products in the culture medium, so that collection of isopropyl alcohol from the culture medium is difficult, which has been problematic in the industrial production of isopropyl alcohol.

The present invention was made under the above-described circumstances, and aims to provide: a bacterium which generates less by-product alcohols and is capable of producing isopropyl alcohol which is more highly purified, without requiring a special step for separating the by-product alcohols; a method for producing isopropyl alcohol using this bacterium; and an apparatus for producing isopropyl alcohol.

Means for Solving the Problems

The first aspect of the present invention is an isopropyl alcohol-producing bacterium to which an acetoacetate decarboxylase activity, an isopropyl alcohol dehydrogenase activity, a CoA transferase activity and a thiolase activity have been imparted, and which can produce isopropyl alcohol from a plant-derived material.

In preferable embodiments of the first aspect of the present invention, each of the acetoacetate decarboxylase activity, the isopropyl alcohol dehydrogenase activity, the CoA transferase activity and the thiolase activity are respectively obtained by introduction of a gene encoding an enzyme derived from at least one selected from the group consisting of a bacterium of the genus *Clostridium*, a bacterium of the genus *Bacillus* and a bacterium of the genus *Escherichia*.

The second aspect of the present invention is a method for producing isopropyl alcohol, the method comprising producing isopropyl alcohol from a plant-derived material using the isopropyl alcohol-producing bacterium.

Preferable embodiments of the second aspect of the present invention comprises: culturing the isopropyl alcohol-producing bacterium while supplying a gas to the mixture comprising the isopropyl alcohol-producing bacterium and the plant-derived material; and collecting isopropyl alcohol produced by the culture The third aspect of the present invention is an isopropyl alcohol-producing apparatus comprising: a culturing unit comprising a mixture comprising the isopropyl alcohol-producing bacterium and the plant-derived material; a gas-supplying unit which is connected to the culturing unit and opens at a position in the mixture contained in the culturing unit, to supply the gas to the mixture; a capture unit comprising the capture liquid which captures isopropyl alcohol; and a connecting unit which connects the culturing unit with the capture unit and allows isopropyl alcohol evaporated in the culturing unit to move to the capture unit.

BRIEF DESCRIPTION OF THE DRAWING

FIG. 1 is a conceptual diagram showing an exemplary embodiment of the isopropyl alcohol-producing apparatus of the invention.

BEST MODE FOR CARRYING OUT THE INVENTION

The isopropyl alcohol-producing bacterium of the invention, to which an acetoacetate decarboxylase activity, an isopropyl alcohol dehydrogenase activity, a CoA transferase activity and a thiolase activity have been imparted, is capable of producing isopropyl alcohol from a plant-derived material.

The method of the invention for producing isopropyl alcohol includes production of isopropyl alcohol from a plant-derived material using the isopropyl alcohol-producing bacterium.

The isopropyl alcohol-producing apparatus of the invention has at least: a culturing unit containing at least a mixture containing at least the isopropyl alcohol-producing bacterium and plant-derived material; a gas-supplying unit which is connected to the culturing unit and opens at a position in the mixture contained in the culturing unit, to supply the gas to the mixture; a capture unit containing at least the capture liquid which captures isopropyl alcohol; and a connecting unit which connects the culturing unit with the capture unit and allows isopropyl alcohol evaporated in the culturing unit to move to the capture unit.

When a range of numerical values is shown in the present specification, unless specifically indicated, the first and second values of the range represent minimum and maximum values, respectively.

Further, in the present specification, a "step" means a stage at which the expected effect of this step is attained, and the concept of the step in this specification also includes cases where the step may not be clearly distinguished from others, such as cases where a plurality of stages proceed simultaneously.

In the present specification, "vvm" indicates the ratio of the volume of a gas to be supplied, per minute, relative to a volume of a liquid; for example, if 2 vvm of a gas is supplied to 10 L of a culture medium, 20 L/minute of the gas is to be supplied.

The invention will now be described.

Isopropyl Alcohol-Producing Bacterium

The isopropyl alcohol-producing bacterium of the invention is an isopropyl alcohol-producing bacterium to which an acetoacetate decarboxylase activity, an isopropyl alcohol dehydrogenase activity, a CoA transferase activity and a thiolase activity have been imparted and is capable of producing isopropyl alcohol from a plant-derived material.

All of the four kinds of isopropyl alcohol-producing enzymes, that is, acetoacetate decarboxylase, isopropyl alcohol dehydrogenase, CoA transferase and thiolase has been imparted to the isopropyl alcohol-producing bacterium of the invention. The present inventors discovered that production of isopropyl alcohol using this isopropyl alcohol-producing bacterium does not generate alcohols such as butanol and ethanol as by-products. Thereby, collection of isopropyl alcohol can be made remarkably simple compared to uses of a conventional isopropyl alcohol-producing microorganism.

In the invention, the plant-derived material is not particularly restricted as long as it is a carbon source obtained from a plant and capable of being metabolized by a bacterium and converted to isopropyl alcohol. In the invention, the plant-derived material may refer to an organ such as a root, stem, stalk, branch, leaf, flower or seed, a plant body containing these, or a degradation product of each of these plant organs, and, in addition, among the carbon sources obtained from plant bodies or plant organs or degradation products thereof, those capable of being used by microorganisms as carbon sources for culturing are also included in the plant-derived materials.

Examples of the carbon sources included in the plant-derived materials generally include saccharides such as starch, glucose, fructose, sucrose, xylose and arabinose; plant degradation products containing large amounts of these components; and hydrolysates of cellulose. Glycerin and fatty acids also correspond to the carbon sources according to the invention.

Preferable examples of the plant-derived material used in the invention include crops such as cereals, maize, rice, wheat, soybean, sugarcane, beet and cotton. Examples of the forms of their usage as raw materials include, but are not limited to, crude products, juices and ground products. The form of the plant-derived materials may also be solely the above-described carbon source.

The isopropyl alcohol-producing bacterium of the invention may be any one as long as it has an ability to produce isopropyl alcohol from these plant-derived materials, and examples thereof include bacteria which utilize plant-derived materials when cultured and secrete isopropyl alcohol into the culture medium after certain time periods.

Four kinds of isopropyl alcohol-producing activities, that is, an acetoacetate decarboxylase activity, an isopropyl alcohol dehydrogenase activity, a CoA transferase activity and a thiolase activity are imparted to the isopropyl alcohol-producing bacterium of the invention.

In the invention, "impart(ing)" an activity, in addition to introducing a gene encoding an enzyme from the outside of a host bacterium into the inside thereof, also includes enhancing the activity of a promoter an enzyme gene retained in the genome of a host bacterium, and replacing a promoter with another promoter to cause overexpression of an enzyme gene.

Acetoacetate decarboxylase referred in the invention is the collective name of enzymes which are classified as the enzyme code 4.1.1.4 according to the report by International Union of Biochemistry (I.U.B.) Enzyme Commission and catalyze reactions producing acetone from acetoacetic acid.

Examples of such enzymes include those derived from bacteria of the genus *Clostridium* such as *Clostridium acetobutylicum* and *Clostridium beijerinckii*; and those derived from bacteria of the genus *Bacillus* such as *Bacillus polymyxa*.

As the gene of acetoacetate decarboxylase which is introduced into the host bacterium of the invention, a DNA having a base sequence of the gene encoding acetoacetate decarboxylase obtained from each of the above-mentioned organisms, or a synthetic DNA sequence synthesized based on a known base sequence(s) of the gene may be used. Preferable examples of the gene include those derived from bacteria of the genus *Clostridium* or bacteria of the genus *Bacillus*, and examples thereof include DNAs having a base sequence of the gene derived from *Clostridium acetobutylicum* or *Bacillus polymyxa*. A DNA having a base sequence of the gene derived from *Clostridium acetobutylicum* is especially preferable.

The isopropyl alcohol dehydrogenase referred in the invention is the collective name of enzymes which are classified as the enzyme code 1.1.1.80 according to the report by International Union of Biochemistry (I.U.B.) Enzyme Commission and catalyze reactions producing isopropyl alcohol from acetone.

Examples of such enzymes include those derived from bacteria of the genus *Clostridium* such as *Clostridium beijerinckii*.

As the gene of isopropyl alcohol dehydrogenase which is introduced into the host bacterium employed in the invention, a DNA having a base sequence of the gene encoding isopropyl alcohol dehydrogenase obtained from each of the above-mentioned organisms or a synthetic DNA sequence synthesized based on a known base sequence(s) of the gene may be used. Preferable examples of the gene include those derived from bacteria of the genus *Clostridium*, and examples thereof include DNAs having a base sequence of the gene derived from *Clostridium beijerinckii*.

The CoA transferase referred in the invention is the collective name of enzymes which are classified as the enzyme code 2.8.3.8 according to the report by International Union of Biochemistry (I.U.B.) Enzyme Commission and catalyze reactions producing acetoacetic acid from acetoacetyl-CoA.

Examples of such enzymes include those derived from bacteria of the genus *Clostridium* such as *Clostridium acetobutylicum* and *Clostridium beijerinckii*, bacteria of the genus *Roseburia* such as *Roseburia intestinalis*, bacteria of the genus *Faecalibacterium* such as *Faecalibacterium prausnitzii*, bacteria of the genus *Coprococcus*, trypanosomes such as *Trypanosoma brucei* and bacteria of the genus *Escherichia* such as *Escherichia coli* (*E. coli*).

As the gene of CoA transferase which is introduced into the host bacterium of the invention, a DNA having a base sequence of the gene encoding CoA transferase obtained from each of the above-mentioned organisms or a synthetic DNA sequence synthesized based on a known base sequence(s) of the gene may be used. Preferable examples of the gene include DNAs having a base sequence of the gene derived from bacteria of the genus *Clostridium* such as *Clostridium acetobutylicum*, bacteria of the genus *Roseburia* such as *Roseburia intestinalis*, bacteria of the genus *Faecalibacterium* such as *Faecalibacterium prausnitzii*, bacteria of the genus *Coprococcus*, trypanosomes such as *Trypanosoma brucei* and bacteria of the genus *Escherichia* such as *Escherichia coli*. More preferable examples thereof include those derived from bacteria of the genus *Clostridium* and bacteria of the genus *Escherichia*. A DNA having a base sequence of the gene derived from *Clostridium acetobutylicum* or *Escherichia coli* is especially preferable.

The thiolase referred in the invention is the collective name of enzymes which are classified as the enzyme code 2.3.1.9 according to the report by International Union of Biochemistry (I.U.B.) Enzyme Commission and catalyze reactions producing acetoacetyl-CoA from acetyl-CoA.

Examples of such enzymes include those derived from bacteria of the genus *Clostridium* such as *Clostridium acetobutylicum* and *Clostridium beijerinckii*, bacteria of the genus *Escherichia* such as *Escherichia coli*, bacteria of *Halobacterium* sp., bacteria of the genus *Zoogloea* such as *Zoogloea ramigera*, bacteria of *Rhizobium* sp., bacteria of the genus *Bradyrhizobium* such as *Bradyrhizobium japonicum*, bacteria of the genus *Caulobacter* such as *Caulobacter crescentus*, bacteria of the genus *Streptomyces* such as *Streptomyces collinus*, bacteria of the genus *Enterococcus* such as *Enterococcus faecalis*, yeasts of the genus *Candida* such as *Candida tropicalis*, the genus *Helianthus* (Asteraceae) such as *Helianthus annuus*, the genus *Gallus* (Phasianidae) such as *Gallus gallus*, the genus *Rattus* (Muridae) such as *Rattus norvegicus*, the genus *Sus* (Suidae) such as *Sus scrofa* and the genus *Bos* (Bovidae) such as *Bos taurus*.

As the gene of thiolase which is introduced into a host bacterium used in the invention, a DNA having a base sequence of the gene encoding thiolase obtained from each of the above-mentioned organisms or a synthetic DNA sequence synthesized based on a known base sequence(s) of the gene may be used. Preferable examples of the gene include DNAs having a base sequence of the gene derived from bacteria of the genus *Clostridium* such as *Clostridium acetobutylicum* and *Clostridium beijerinckii*, bacteria of the genus *Escherichia* such as *Escherichia coli*, bacteria of *Halobacterium* sp., bacteria of the genus *Zoogloea* such as *Zoogloea ramigera*, bacteria of *Rhizobium* sp., bacteria of the genus *Bradyrhizobium* such as *Bradyrhizobium japonicum*, bacteria of the genus *Caulobacter* such as *Caulobacter crescentus*, bacteria of the genus *Streptomyces* such as *Streptomyces collinus*, bacteria of the genus *Enterococcus* such as *Enterococcus faecalis*, yeasts of the genus *Candida* such as *Candida tropicalis*, the genus *Helianthus* (Asteraceae) such as *Helianthus annuus*, the genus *Gallus* (Phasianidae) such as *Gallus gallus*, the genus *Rattus* (Muridae) such as *Rattus norvegicus*, the genus *Sus* (Suidae) such as *Sus scrofa* and the genus *Bos* (Bovidae) such as *Bos taurus*. More preferable examples thereof include those derived from bacteria of the genus *Clostridium* and bacteria of the genus *Escherichia*; and a DNA having a base sequence of the gene derived from *Clostridium acetobutylicum* or *Escherichia coli* is especially preferable.

Among these, each of the above four kinds of enzymes is preferably derived from at least one species selected from the group consisting of bacteria of the genus *Clostridium*, bacteria of the genus *Bacillus* and bacteria of the genus *Escherichia* in view of the enzyme activity, and, in particular, more preferable are the cases where acetoacetate decarboxylase and isopropyl alcohol dehydrogenase are derived from a bacterium/bacteria of the genus *Clostridium* and the CoA transferase activity and thiolase activity are derived from a bacterium/bacteria of the genus *Escherichia*, and the cases where all of these four kinds of enzymes are derived from a bacterium/bacteria of the genus *Clostridium*.

In particular, each of the four kinds of enzymes according to the invention is preferably derived from any of *Clostridium acetobutylicum*, *Clostridium beijerinckii* and *Escherichia coli* in view of the enzyme activity. More preferably, acetoacetate decarboxylase is the enzyme derived from *Clostridium acetobutylicum*; each of CoA transferase and thiolase is the enzyme derived from *Clostridium acetobutylicum* or *Escherichia coli*; and isopropyl alcohol dehydrogenase is the enzyme derived from *Clostridium beijerinckii*. Especially preferably, in view of the enzyme activities of the above-described four kinds of enzymes, the acetoacetate decarboxylase activity is derived from *Clostridium acetobutylicum*; the isopropyl alcohol dehydrogenase activity is derived from *Clostridium beijerinckii*; and the CoA transferase activity and thiolase activity are derived from *Escherichia coli*.

The activity of each of these enzymes in the invention may be introduced from the outside of the host bacterium into the inside of the host bacterium, or alternatively, the activity of each of these enzymes in the invention may be realized by overexpression of the enzyme genes by enhancement of activity of a promoter(s) of the enzyme genes retained in the genome of the host bacterium or replacement of the promoter(s) with another promoter(s) to cause overexpression of the enzyme gene.

Introduction of the enzyme activities may be carried out, for example, by introduction of the genes encoding those four kinds of enzymes from the outside of the host bacterium into the inside of the host bacterium using gene recombination technology. In this case, the introduced enzyme genes may be either those from the same or different from the species of the host cell. Preparation of the genomic DNA, cleavage and ligation of a DNA, transformation, PCR (Polymerase Chain Reaction), design and synthesis of oligonucleotides used as primers, and the like may be carried out by the conventional methods well-known by persons skilled in the art. These methods are described in, for example, Sambrook, J., et al., "Molecular Cloning A Laboratory Manual, Second Edition", Cold Spring Harbor Laboratory Press (1989).

Any promoter may be used as the promoter used for enhancement of the promoter activity or overexpression of the enzyme gene as long as it can be expressed in a host such as *E. coli*. For example, promoters derived from *E. coli* or phages, such as the trp promoter, lac promoter, $P_L$ promoter and $P_R$ promoter are used. Promoters artificially designed or modified, such as the tac promoter may also be used. And, as described in Examples of the invention, the glyceraldehyde-3-phosphate dehydrogenase (GAPDH) promoter, glutamate decarboxylase A (gadA) promoter and serine hydroxymethyltransferase (glyA) promoter may also be used. These may be appropriately selected depending on the origins and types of the enzymes used.

For example, for enhancement of the activity of thiolase or CoA transferase derived from *Escherichia coli*, any promoter(s) may be used as long as it/they allow(s) expression of the enzyme in a host such as *E. coli*, and one or more of the promoter may be appropriately selected from the group of exemplary promoters consisting of the trp promoter, lac promoter, $P_L$ promoter, $P_R$ promoter, tac promoter, glyceraldehyde-3-phosphate dehydrogenase (GAPDH) promoter, glutamate decarboxylase A (gadA) promoter and serine hydroxymethyltransferase (glyA) promoter. Promoters such as the trp promoter, lac promoter, $P_L$ promoter, $P_R$ promoter, tac promoter, glyceraldehyde-3-phosphate dehydrogenase (GAPDH) promoter, glutamate decarboxylase A (gadA) promoter and serine hydroxymethyltransferase (glyA) promoter may be used to replace the promoter for thiolase or CoA transferase derived from *Escherichia coli*.

These promoters may be introduced into the host cell according to a conventional method such that the target enzyme gene may be expressed by, for example, ligating the promoter(s) with a vector which is the same one with which the target enzyme gene is ligated, followed by introduction of the vector into the host cell together with the enzyme gene.

In the invention, the host bacterium is a prokaryote which is used for introduction of the genes encoding the four kinds of enzymes of acetoacetate decarboxylase, isopropyl alcohol dehydrogenase, CoA transferase and thiolase, or a prokaryote which is the target of either enhancement of activity of promoter(s) of these enzymes or replacement of the promoter(s). Examples of such a bacterium include bacteria of the genus *Escherichia*, bacteria of the genus *Bacillus* and bacteria of the genus *Corynebacterium*; and *Escherichia coli*, which is especially convenient and has yielded plenty of results in industrial uses, is preferably used.

Method for Production of Isopropyl Alcohol

The method for production of isopropyl alcohol of the invention includes producing isopropyl alcohol from a plant-derived material using the isopropyl-alcohol producing bacterium of the invention.

Thereby, it is possible to produce isopropyl alcohol having high purity without generating other alcohols as by-products. Thus, according to the invention, it is possible to produce isopropyl alcohol easily and efficiently without requiring a complicated process for separation of by-product alcohols.

This production method includes a method including assimilating a plant-derived material by culturing the isopropyl alcohol-producing bacterium in a mixture containing the isopropyl alcohol-producing bacterium and the plant-derived material, and, after a certain period of time, purifying isopropyl alcohol secreted in the culture medium using a known technique(s) such as distillation, membrane separation and extraction.

The mixture in the production method of isopropyl alcohol may contain mainly a basal medium generally used for culturing bacteria, and any medium may be used as long as it is a medium normally used depending on the type of the isopropyl alcohol-producing bacterium.

Such a basal medium is not particularly limited as long as it is a medium containing a carbon source, nitrogen source, inorganic ions and, as required, other minor components. As the carbon source, saccharides such as glucose, fructose and/or molasses; organic acids such as fumaric acid, citric acid and/or succinic acid; alcohols such as methanol, ethanol and/or glycerol; and/or the like may be appropriately used.

As the nitrogen source, inorganic or organic nitrogen sources such as organic ammonium salts, inorganic ammonium salts, nitrate nitrogen, ammonia gas, aqueous ammonia and/or protein hydrolysates; and/or the like may be appropriately used. As the inorganic ions, magnesium ions, phosphate ions, potassium ions, iron ions, manganese ions and/or the like may be appropriately used as required.

As an organic minor component(s), vitamins, amino acids, and/or yeast extract, peptone, polypeptone, corn steep liquor, casein digest and/or the like containing vitamins, amino acids, and/or the like may be appropriately used.

Polypeptone is a resultant obtained by hydrolyzing protein by an enzyme or acid, and all of its nitrogen source may be regarded as those derived from the protein, although there are cases where a small amount of ammonia nitrogen measured according to the analytical value of polypeptone LotO586A from Nihon Pharmaceutical Co., Ltd is generated. The components of polypeptone include, for example: 12.5% by mass to 14.5% by mass of nitrogen content in total; 5.0% by mass to 6.5% by mass of amino nitrogen; 4.0% by mass to 7.0% by mass of superheat residual; and 3.5% by mass to 5.5% by mass of loss lost by drying, based on the total mass of the polypeptone. Normally, the content of the polypeptone in a medium is in the range of from 0.02 to 2% (w/w), and preferably in the range of from 0.1 to 1% (w/w).

Corn steep liquor is obtained by concentrating an immersion fluid which contains soluble components eluted during soaking of maize and components produced by lactic acid fermentation. According to Microbiol. Mol. Biol. Rev., December 1948; Vol. 12: pp. 297-311, its components are, for example: 45% by mass to 55% by mass of water; 2.7% by mass to 4.5% by mass of the total nitrogen content; 1.0% by mass to 1.8% by mass of amino nitrogen; 0.15% by mass to 0.40% by mass of volatile nitrogen; 0.1% by mass to 11.0% by mass of reducing sugars; 5% by mass to 15% by mass of lactic acid; 9% by mass to 10% by mass of the ash content; 0.1% by mass to 0.3% by mass of volatile acids; and 0.009% by mass to 0.015% by mass of sulfur dioxide, based on the total mass of the corn steep liquor. According to the above components, there is a possibility that nitrogen-containing compounds of up to 0.40% (w/w) which may produce ammonium ions in water are contained as the volatile nitrogen; however, even in cases where these are entirely ammonium ions, the ammonium ion content is only 0.008% in a medium containing 2% of corn steep liquor. Corn steep liquor is normally used at a concentration within the range of 0.1 to 20% (w/w), and preferably used at a concentration within the range of 0.5 to 7% (w/w).

Yeast extract has been disclosed as containing amino acids, polymers thereof, nucleic acids, vitamins, organic acids and inorganic salts, and, according to the analysis data (Catalog #211929, 211931, 211930) of the yeast extract by BD (Becton, Dickinson and Company), inorganic salts including calcium, magnesium, potassium, sodium, chloride, sulfuric acid or phosphoric acid are described, but there is no description of compounds which may produce ammonium ions. Components of yeast extract are, for example: 11.4% by mass of the total nitrogen content; 6.9% by mass of amino nitrogen; 13.1% by mass of the ash content; 1.0% by mass of loss lost by drying; 0.2% by mass of sodium chloride; and 10.5% by mass of the total inorganic salts, based on the total mass of the yeast extract.

The amount of the plant-derived material in the mixture varies depending on its type and the activity and number of isopropyl alcohol-producing bacteria contained in the mixture. In general, the starting sugar concentration may be 20% by mass or less in terms of glucose, and may be preferably 15% by mass less, relative to the total mass of the mixture, in view of the sugar tolerance of the bacteria. Each of other components may be added at an amount at which it is normally added to media for microorganisms, and there is no limitation thereto.

A compound containing nitrogen can be preferably further added to the mixture containing the isopropyl alcohol-producing bacteria and plant-derived material, in view of improvement of productivity of isopropyl alcohol. "Further added" means that a nitrogen-containing compound which may generate an ammonium ion in water is contained in the mixture at a content higher than that contained in a common culture medium. Thereby, the isopropyl alcohol-producing bacteria can be cultured in a culture medium containing a nitrogen-containing compound(s) other than amino acids at a higher concentration than that/those under a normal culture condition. The timing when the nitrogen-containing compound other than amino acids is added to the culture medium may be either before starting the culture or during the culture.

Examples of the nitrogen-containing compound which may produce an ammonium ion in water include: inorganic and organic compounds having ammonium salts such as ammonium sulfate and ammonium nitrate; ammonia gas; and aqueous ammonia. The nitrogen-containing compounds which may produce an ammonium ion in water are contained at 0.02% (w/w) in M9, that is a common medium for bacteria, and at 0.02% (w/w) in MS, that is another common medium. In the invention, the culture medium may contain the nitrogen-containing compound at a higher amount than these in order to increase the yield of isopropyl alcohol. In the invention, in view of enhancement of the productivity of isopropyl alcohol, the nitrogen-containing compound which may produce an ammonium ion in water is preferably added before culturing such that the total mass of the nitrogen atoms in the compound becomes 0.04% to 10.6% (w/w) relative to the total mass of the culture medium at the beginning of the culturing of the mixture. The total mass of the nitrogen atoms is more preferably 0.04% to 5.30% (w/w), especially preferably 0.04% to 4.24% (w/w). In this case, 1 mL of liquid is assumed to weigh 1 g.

In addition, the culture medium may contain other additive components which are usually added to media for microorganisms, such as antibiotics, at concentrations at which they are usually used. An antifoaming agent is preferably added to the culture medium at an appropriate amount for suppressing foaming.

Examples of the medium used in the invention include: liquid media based on an aqueous medium; and solid media based on a solid phase such as agarose. The medium is preferably a liquid medium, considering that it is subjected to industrial production. Examples of the aqueous medium which forms the liquid medium include those usually used, such as distilled water and buffers.

There is no particular limitation to the culture condition employed for the culturing in the invention. In embodiments, the culturing may be carried out under an aerobic condition with appropriately controlling pH and temperature so that the pH becomes in the range of 4 to 9, which is preferably in the range of 6 to 8, and the temperature becomes in the range of 20° C. to 50° C., which is preferably in the range of 25° C. to 42° C.

The method for collection of isopropyl alcohol accumulated in the culture medium is not particularly limited, and examples thereof include a method in which bacterial cells are removed from the culture medium by centrifugation or the like and isopropyl alcohol is then separated by a normal separation method such as distillation or membrane separation.

The method of the invention for production of isopropyl alcohol may include preculturing to attain an appropriate bacterial cell number and/or an appropriate level of the active state of the isopropyl alcohol-producing bacteria to be used, before the culturing for producing isopropyl alcohol. The preculturing may employ a culture condition which is normally used and depends on the type of the isopropyl alcohol-producing bacteria.

The method for production of isopropyl alcohol of the invention preferably includes: culturing the isopropyl alcohol-producing bacterium with supplying a gas to a mixture containing the isopropyl alcohol-producing bacterium and the plant-derived material; and collecting isopropyl alcohol produced by the culture.

According to this method, the producing bacteria are cultured with the supplying of a gas to a mixture (aeration culture). Due to the aeration culture, produced isopropyl alcohol is released into the mixture and evaporates from the mixture, and, as a result, the produced isopropyl alcohol can be easily separated from the mixture (medium). Since the produced isopropyl alcohol is continuously separated from the mixture, an increase of the concentration of isopropyl alcohol in the mixture can be suppressed. Consequently, there is no need to consider the resistance of the isopropyl alcohol-producing bacteria to isopropyl alcohol.

The gas supplied to the mixture in the culturing may be a gas containing oxygen. Examples thereof include oxygen, the air, and a mixed gas containing one of these and an inert gas(es). These gases are preferably sterilized.

Examples of the inert gas which may be used include $N_2$ gas and rare gases (such as Ar, He, Ne, Kr, or Xe), and, among these, in view of handling, $N_2$ gas and Ar gas are preferable, and $N_2$ gas is more preferable.

When a mixed gas is used, the mixing ratio may be arbitrary as long as the bacteria to be cultured do not lose their physiological activities. In embodiments, the mixing ratio of the inert gas(es) is preferably in the range of from 10 to 90% based on the total mass of the mixed gas to allow processing for a long period by appropriately suppressing the activity of the isopropyl alcohol-producing bacteria.

A porous body such as a ceramics body may be placed in a specific mixture to ensure aeration in the mixture.

The amount of the gas to aerate the mixture is not limited. When only the air is used as the gas, aeration is generally carried out at 0.02 vvm to 2.0 vvm (vvm; aeration volume [mL]/liquid volume [mL]/time period [minute]), preferably at 0.1 vvm to 1.5 vvm in view of suppressing physically damaging the bacteria.

The culturing is preferably carried out with stirring the entire mixture. Thereby, the isopropyl alcohol-producing bacteria and the plant-derived material are well mixed with each other, and the gas supplied into the mixture is allowed to efficiently diffuse to the entire mixture.

The culturing may be continued from the beginning of the culture until the plant-derived material is consumed, or until the activity of the isopropyl alcohol-producing bacteria is lost. The time period of the culturing varies depending on the number and activity of the isopropyl alcohol-producing bacteria as well as the amount of the plant-derived material, and may be generally 1 hour or more, and be preferably 4 hours or more. On the other hand, although the culturing period may be unlimitedly extended by further providing the plant-derived material and/or the isopropyl alcohol-producing bacteria, it may be generally 5 days or less, preferably 55 hours or less, in view of the processing efficiency.

In the collecting, isopropyl alcohol produced in the culturing and separated from the mixture is collected. The method for the collecting may be generally one by which isopropyl alcohol which is in the form of gas distilled from the mixture by culturing or in the form of droplets can be collected. Examples of such a method include collection into a collecting unit such as a generally-used closed container. Particularly, in view of ability to collect isopropyl alcohol solely at a high purity, the method preferably includes contacting, with isopropyl alcohol separated from the mixture, a capture liquid which captures isopropyl alcohol.

Examples of the capture liquid for capturing isopropyl alcohol include water and organic solvents. The organic solvent as the capture liquid is not limited as long as it allows isopropyl alcohol to dissolve easily thereinto and it has a boiling point with which it can be separated from isopropyl alcohol when it is distilled in the aqueous or absolute (non-water containing) state. Examples of such an organic solvent include toluene, dimethylformamide and dimethyl sulfoxide. The organic solvent as the capture liquid may be used with being mixed with water as appropriate.

The capture liquid is preferably water. Since volatile impurities expected to be produced together with isopropyl alcohol are less soluble in water than isopropyl alcohol, water may enable to efficiently separate isopropyl alcohol from the impurities and collect the isopropyl alcohol.

Contacting of isopropyl alcohol with the capture liquid may be carried out for a length of time which is sufficient for isopropyl alcohol to be dissolved in the capture liquid. Dissolution of isopropyl alcohol into the capture liquid is not time-consuming as long as the capture liquid is water or the above-mentioned organic solvent, and usually sufficiently attained in about 2 hours.

To promote dissolution of isopropyl alcohol into the capture liquid, it is preferable to directly inject, to the capture liquid, isopropyl alcohol which was separated from the mixture and is in the form of gas or droplets. This injection causes bubbling, which accelerates dissolution of isopropyl alcohol to the capture liquid.

The method of the invention for producing isopropyl alcohol preferably includes liquefying isopropyl alcohol separated from the mixture before contacting the isopropyl alcohol with the capture liquid, in order to increase the collection efficiency.

The method for liquefaction of isopropyl alcohol may be any method as long as it enables to liquefy isopropyl alcohol which is in the form of gas or droplets, and examples thereof include cooling of isopropyl alcohol to an extent sufficient for a phase change of isopropyl alcohol. Examples of the cooling method include air cooling and methods using cooled water or alcohols.

Isopropyl alcohol separated from the mixture may be collected using an adsorbent. Examples of such an adsorbent include porous bodies such as zeolite and silica gel, which are normally used for adsorption of liquid or gas.

According to this method for producing isopropyl alcohol, isopropyl alcohol can be collected in the state dissolved in the capture liquid or in the mixture. The collected isopropyl alcohol can be confirmed using a normal detection method such as HPLC. The collected isopropyl alcohol can be further purified as required. Examples of such a purification method include distillation.

In cases where the collected isopropyl alcohol is in the state of an aqueous solution, this method for producing isopropyl alcohol may further include dehydrating in addition to the collecting. Dehydration of isopropyl alcohol may be carried out by a conventional method.

FIG. 1 is a conceptual diagram showing an example of the production apparatus 10 applicable to the method of the invention for production of isopropyl alcohol. This method for production of isopropyl alcohol will be described by reference to FIG. 1.

The production apparatus 10 has a culture vessel 12 and a trap vessel 40, and the culture vessel 12 and trap vessel 40 are connected to each other via a connecting duct 30. The culture vessel 12 and trap vessel 40 are capable of being sealed so as not to allow leakage of the internal atmosphere to the outside of the vessels.

In the culture vessel 12, a mixture 14 containing isopropyl alcohol-producing bacteria B and a plant-derived material M is placed. The amount of the mixture 14 placed may be about a half of the capacity of the culture vessel 12, which amount may be adjusted as appropriate depending on the capacity of the culture vessel 12 and/or the scale of the production apparatus 10. The culture vessel 12 may be formed from substances normally used for industrial production of materials using microorganisms, and is not particularly limited. The production apparatus 10 may be capable of performing processing at a standard temperature and pressure, and may be further equipped with a heating device and/or a pressurizing device as required to allow heating and/or pressurizing.

An injection duct 16 for injecting a gas from the outside of the apparatus is connected to the culture vessel 12. One terminal of the injection duct 16 is connected to an aeration apparatus, which is provided in the outside of the production apparatus 10 and is not shown in the FIGURE. Another terminal of the injection duct 16 opens at a position which is in the vicinity of the bottom of the culture vessel 12 and is inside the culture vessel 12. The volume of the mixture 14 is adjusted in advance such that the liquid level of the mixture 14 placed in the culture vessel 12 is above the opening of the injection duct 16.

The culture vessel 12 has a motor unit 22 provided in the outside of the culture vessel 12 and a stirring device 20 provided with a stirring unit 24 connected to the motor unit 22. The stirring unit 24 is in the shape of propeller blades or the like, and placed in the vicinity of the bottom of the culture vessel 12.

A drive control device, which is not shown in the FIGURE, is connected to the motor unit 22 and controls driving of the motor unit 22 such that the stirring unit 24 is rotated at a certain rotation speed. The rotation speed of the stirring unit 24 is not particularly limited, and stirring is generally carried out at 100 rpm to 1,000 rpm, preferably 200 rpm to 800 rpm.

A trap liquid 42 as the capture liquid is placed inside the trap vessel 40. On the top of the trap vessel 40, an exhaust duct 44 for exhausting gas in the trap vessel 40 to the outside of the trap vessel 40 is connected.

One terminal of the connecting duct 30 opens in the upper section of the culture vessel, allowing the gas placed in the culture vessel 12 to be guided to the outside of the culture vessel 12. Another terminal of the connecting duct 30 is elongated to and opens at the vicinity of the bottom section of the trap vessel 40, and the liquid level of the capture liquid placed in the trap vessel 40 is adjusted in advance such that it is above the opening section of the connecting duct 30.

The connecting duct 30 may have a cooler which positively cools the inside of the connecting duct 30. Thereby, when the gas passes through the connecting duct 30, the gas can be positively liquefied.

The effect of this production apparatus will be described below.

The mixture 14 containing the isopropyl-alcohol-producing bacteria B and the plant-derived material M is injected into the culture vessel 12 of the production apparatus 10 such that the liquid level of the mixture 14 reaches a portion sufficiently above the terminal of the injection duct 16. The motor section 22 of the stirring device 20 is powered on to rotate the stirring unit 24 at a certain rotation speed. Addition of the mixture 14 may also be carried out after placing a certain amount of the medium in the culture vessel 12 and adjusting its temperature appropriately in advance, such that a certain total amount is attained.

A certain amount of the mixture 14 is placed in the culture vessel 12, and the aeration apparatus, which is not shown in the FIGURE, is powered on to inject the gas into the culture vessel 12. Thereby, in the culture vessel 12, the gas is injected into the mixture, and aeration culture starts.

When the aeration culture starts, the isopropyl alcohol-producing bacteria B begin production of isopropyl alcohol by assimilating the plant-derived material. The produced isopropyl alcohol is released from the bacterial cells into the mixture, and a part of the isopropyl alcohol is dissolved into the mixture while it is mostly evaporates from the mixture. Thereby, isopropyl alcohol is separated from the mixture. The isopropyl alcohol separated from the mixture moves from the upper section of the culture vessel 12 to enter into the connecting duct 30 as exhaust, to further move into the trap vessel 40.

When passing through the connecting duct 30, a part of the isopropyl alcohol in the exhaust is cooled and liquefied.

The isopropyl alcohol which is being exhausted and moved to the trap vessel 40 enters into the trap vessel 40 from another terminal of the connecting duct 30 which opens in the bottom section of the trap vessel 40, and is injected into the trap liquid 42. At this time, bubbling occurs in the trap liquid 42 by the injection of the exhaust. At this time, the isopropyl alcohol is dissolved into the trap liquid 42. On the other hand, volatile impurities, which are in the exhaust and moved with the isopropyl alcohol from the culture vessel 12 to the trap vessel 40, are less soluble to the trap liquid 42, so that they are released from the trap liquid 42 and exhausted to the outside of the trap vessel 40 as the final exhaust, through the exhaust duct 44 opening in the top section of the trap vessel 40.

The amount of isopropyl alcohol produced in the culture vessel 12 is confirmed by collection using a collection machinery, which is not shown in the FIGURE, and the process is terminated when production of isopropyl alcohol is confirmed to be ended or decreased, or after a certain time period.

The trap liquid 42 after the processing has a high concentration of isopropyl alcohol dissolved therein. Therefore, it can be collected as an isopropyl alcohol solution at a high concentration. This trap liquid 42 may be collected to further isolate and purify isopropyl alcohol as required. Since a partial portion of isopropyl alcohol is dissolved in the mixture 14 in the culture vessel 12, the mixture 14 can be collected to isolate and purify isopropyl alcohol as required.

Thus, by using the production apparatus 10, isopropyl alcohol produced using the isopropyl alcohol-producing bacteria may be separated and collected at an ordinary temperature and pressure for example, at 25° C. and 101,325 Pa). Accordingly, the production apparatus can have a simple structure, and it is not necessary to provide a complicated separation step and/or purification step.

Symbols in FIG. 1 will be described. The number 10 indicates the production apparatus (isopropyl alcohol-producing apparatus), the number 12 indicates the culture vessel (culturing unit), the number 14 indicates the mixture, the number 16 indicates the injection duct (gas-supplying unit), the number 20 indicates the stirring device (stirring unit), the number 30 indicates the connecting duct (connecting unit), the number 40 indicates the trap vessel (capture unit), the number 42 indicates the trap liquid (capture liquid), and the number 44 indicates the exhaust duct.

The shape of respective parts and units, such as the culture vessel 12, trap vessel 40 and connecting duct 30 provided in the production apparatus 10 may be changed as appropriate as long as its intended effect is not impaired.

An injection unit and/or exhaust unit for continuously injecting the mixture 14 or isopropyl alcohol-producing bacteria into the culture vessel 12 may be provided to the production apparatus 10 of this exemplary embodiment. This allows continuous production of isopropyl alcohol.

In the invention, as mentioned above, isopropyl alcohol which is more highly purified can be produced with less by-product alcohols without requiring a step for separating the by-product alcohols.

In a preferable embodiment of the invention, isopropyl alcohol which is more highly purified can be produced continuously and conveniently.

EXAMPLES

Examples of the invention will now be described below, although the invention is not limited thereby. "%" in the description indicates quantity in terms of mass unless otherwise specified.

Example 1

Construction of Vector for Expression of Isopropyl Alcohol-producing Enzyme Genes Derived from Bacterium of Genus *Clostridium* and Transformant with the Expression Vector Amino acid sequences and base sequences of the genes of the four kinds of isopropyl alcohol-producing enzymes in bacteria of the genus *Clostridium* have been already reported. That is, thiolase is described in 3005963-3007364 of the complementary strand of the genome sequence described in GenBank accession number AE001437. CoA transferase is described in GenBank accession number X72831, acetoacetate decarboxylase is described in GenBank accession number M55392, and isopropyl alcohol dehydrogenase is described in GenBank accession number AF157307. The sequence of the thiolase promoter existing in the above base sequence of thiolase may be used as the sequence of a promoter required for expression of these four kinds of genes.

To obtain the thiolase promoter and the thiolase gene, amplification by PCR was carried out with TTT GAA TTC CAT GAT TTT AAG GGG GTT AGC ATA TGC A (SEQ ID NO:1) and TTT GGT ACC CTA GCA CTT TTC TAG CAA TAT TGC TGT TCC (SEQ ID NO:2) using the genomic DNA of *Clostridium acetobutylicum* ATCC824 as the template. The thus-obtained DNA fragment was digested with the restriction enzymes EcoRI and KpnI to obtain a thiolase fragment having a size of about 1.5 kbp including a DNA sequence encoding the thiolase promoter.

To obtain the CoA transferase gene, amplification by PCR was carried out with TTT GGT ACC CAA CCT TAA ACC TTC ATA TTT CAA CTA CTT (SEQ ID NO: 3) and TTT GGA TCC CTA AAC AGC CAT GGG TCT AAG TTC (SEQ ID NO: 4) using the genomic DNA of *Clostridium acetobutylicum* ATCC824 as the template. The thus-obtained DNA fragment was digested with the restriction enzymes KpnI and BamHI to obtain a CoA transferase fragment having a size of about 1.4 kbp.

To obtain the acetoacetate decarboxylase gene and a terminator sequence, amplification by PCR was carried out with TTT GGA TCC AGC TAA ACA TTA TTA AAT TTA GGA AGG TG (SEQ ID NO: 5) and TTT GTC GAC CCA ATG AAC TTA GAC CCA TGG CTG (SEQ ID NO: 6) using the genomic DNA of *Clostridium acetobutylicum* ATCC824 as the template. The thus-obtained DNA fragment was digested with the restriction enzymes BamHI and Sail to obtain an acetoacetate decarboxylase fragment having a size of about 880 by including a DNA sequence encoding the terminator.

*Clostridium acetobutylicum* ATCC824 can be obtained from American Type Culture Collection, that is a bank of cells, microorganisms and genes.

To obtain the isopropyl alcohol dehydrogenase gene, amplification by PCR was carried out with TTT GGT ACC GCG AAA TAG CGA TGA ACA GGC AG (SEQ ID NO: 7) and TTT GGT ACC GCA GAT TTT GCT ACT CTT GGA GC (SEQ ID NO: 8) using the genomic DNA of *Clostridium beijerinckii* NRRL B-593 as the template. The thus-obtained DNA fragment was digested with the restriction enzyme KpnI to obtain an isopropyl alcohol dehydrogenase fragment having a size of about 1.4 kbp.

*Clostridium beijerinckii* NRRL B-593 can be obtained from VTT Culture Collection, that is a bank of cells and microorganisms.

The four DNA fragments and a fragment obtained by digestion of the plasmid pUC19 with EcoRI and Sail were mixed and ligated using a ligase, and the *Escherichia coli* Strain DH5α competent cell (trade name: DNA-903, manufactured by Toyobo Co. Ltd.) was transformed with the resulting ligation product to obtain transformants growing on a culture medium of LB Broth Miller ((trade name: Difco244620) agar plate which contains 100 μg/mL of ampicillin and having 40 μl each of 40 mg/mL X-gal and 20% IPTG applied onto a surface thereof. The obtained colonies were cultured in an LB liquid medium containing 100 μg/mL of ampicillin at 37° C. overnight, and the plasmid pIPA was collected from the thus-obtained bacterial cells.

An *Escherichia coli* strain B (ATCC11303) competent cell was transformed with this plasmid pIPA and cultured on a culture medium of LB Broth Miller agar plate containing 100 μg/mL of ampicillin at 37° C. overnight to obtain the isopropyl alcohol-producing enzyme genes expression vector transformant strain pIPA/B.

The *Escherichia coli* strain B (ATCC11303) can be obtained from American Type Culture Collection, that is a bank of cells, microorganisms and genes.

Example 2

Production of Isopropyl Alcohol by *Escherichia Coli* Strain pIPA/B and *Escherichia Coli* Wild-Type Strain As preculturing, 5 mL of LB Broth Miller culture medium containing 0.1 g/L of ampicillin and 2 g/L of glucose was placed in a plastic tube having a capacity of 14 mL (trade name: 2057, manufactured by FALCON), and the *Escherichia coli* strain pIPA/B obtained in Example 1 was inoculated thereto, followed by culturing overnight at a culturing temperature of 37° C. with shaking at 120 rpm. The *Escherichia coli* B wild-type strain was cultured with shaking in a medium having the same formulation except that it did not contain ampicillin, under the same culturing condition. The total amount of each of the preculture media was transferred to an Erlenmeyer flask having a capacity of 300 mL and containing 60 mL of LB Broth Miller culture medium with 0.1 g/L of ampicillin and 20 g/L of glucose, to carry out culture. The culturing was carried out at a stirring rate of 120 rpm and a culturing temperature of 37° C. The bacterial cell culture medium was sampled 48 hours after beginning of the culture, and the bacterial cells were removed by centrifugation, followed by measurement of accumulated amounts of isopropyl alcohol, butanol, ethanol and acetone in the thus-obtained culture supernatant according to a conventional method with HPLC. The results are shown in Table 1. Accumulation of 2.1 g/L of isopropyl alcohol was confirmed after 48 hours of culturing of the *Escherichia coli* strain pIPA/B. At this time, there was no accumulation of butanol and ethanol.

TABLE 1

| Results of Measurement by HPLC | | |
|---|---|---|
| | Strain pIPA/B | Wild-type strain |
| Isopropyl alcohol | 2.1 g/L | 0.0 g/L |
| Butanol | 0.0 g/L | 0.0 g/L |
| Ethanol | 0.0 g/L | 0.0 g/L |
| Acetone | 0.1 g/L | 0.0 g/L |

Example 3

Production of Isopropyl Alcohol by *Escherichia Coli* Strain pIPA/B Using 1 L-Culture Vessel (1)

The processing in this Example was carried out using the production apparatus 10 shown in FIG. 1. The culture vessel 12 had a capacity of 1 L, and the trap vessel had a capacity of 500 mL. All of the culture vessel 12, trap vessel 40, injection duct 16, connecting duct 30 and exhaust duct 44 were made of glass. 400 mL of water (trap water) as the trap liquid 42 was injected in the trap vessel 40.

As preculturing, 4 mL of LB Broth Miller culture medium containing 0.1 g/L of ampicillin and 2 g/L of glucose was placed in a test tube, and the *Escherichia coli* strain pIPA/B obtained in Example 1 was inoculated thereto, followed by culturing for 18 hours at a culturing temperature of 37° C. with shaking at 120 rpm. The entire of the preculture medium was inoculated to a 1 L-culture vessel containing 500 mL of LB Broth Miller culture medium containing 0.1 g/L of ampicillin, 20 g/L of glucose and one drop of decanal, and culturing was carried out. This culture was carried out at a stirring rate of 500 rpm and culturing temperature of 37° C., and pH of the culture medium was controlled to 7.0 using 12.5%- ammonia solution. 20 mL of glucose at a concentration of 0.5 g/mL was added 25 hours after beginning of the culture. Samples were taken from the bacterial cell culture 48 hours after beginning of the culturing, and the bacterial cells were removed by centrifugation, followed by measurement of the accumulated amounts of isopropyl alcohol, butanol, ethanol and acetone in the thus-obtained culture supernatant according to a conventional method by HPLC. The results are shown in Table 2. Accumulation of 3.0 g/L of isopropyl alcohol was confirmed after 48 hours of culturing of the *Escherichia coli* strain pIPA/B. At this time, there was no accumulation of butanol and ethanol. Each measured value in Table 2 is the sum of the content of isopropyl alcohol in the culture medium and that in the trap water (400 mL) after culturing.

TABLE 2

Results of Measurement by HPLC

| | Strain pIPA/B |
|---|---|
| Isopropyl alcohol | 3.0 g/L |
| Butanol | 0.0 g/L |
| Ethanol | 0.0 g/L |
| Acetone | 0.9 g/L |

Example 4

Construction of Vector Expressing Thiolase Gene Derived from *Escherichia Coli*, CoA Transferase Gene Derived from *Escherichia Coli*, Acetoacetate Decarboxylase Gene Derived from Bacterium of Genus *Clostridium* and Isopropyl Alcohol Dehydrogenase Gene Derived from Bacterium of Genus *Clostridium*, and Transformant with the Expression Vector Amino acid sequences and base sequences of the genes of thiolase of *Escherichia coli* and CoA transferase of *Escherichia coli* have been already reported. That is, the gene encoding thiolase is described in 2324131-2325315 of the genomic sequence of the *Escherichia coli* Strain MG1655 described in GenBank accession number U00096. The gene encoding CoA transferase is described in 2321469-2322781 of the above-described genomic sequence of the *Escherichia coli* Strain MG1655. Production of isopropyl alcohol is possible by expressing, together with these, the acetoacetate decarboxylase gene and isopropyl alcohol dehydrogenase gene derived from a bacterium/bacteria of the genus *Clostridium*. The promoter sequence of glyceraldehyde-3-phosphate dehydrogenase (which may be hereinafter referred to as GAPDH) described in 397-440 of the base sequence information of GenBank accession number X02662 can be used as the sequence of a promoter required for expression of the above-described genes.

To obtain the GAPDH promoter, amplification by PCR was carried out with CGAGCTACATATGCAATGATTGACAC-GATTCCG (SEQ ID NO: 9) and CGCGCGCATGC-TATTTGTTAGTGAATAAAAGG (SEQ ID NO: 10) using the genomic DNA of the *Escherichia coli* Strain MG1655 as the template. The thus-obtained DNA fragment was digested with the restriction enzymes NdeI and SphI to obtain a DNA fragment corresponding to the GAPDH promoter having a size of about 110 bp. The thus-obtained DNA fragment and a fragment obtained by digestion of the plasmid pBR322 (GenBank accession number J01749) with the restriction enzymes NdeI and SphI were mixed and ligated using a ligase, and the *Escherichia coli* strain DH5α competent cell (trade name: DNA-903, manufactured by Toyobo Co. Ltd.) was transformed with the resulting ligation product to obtain transformants growing on an LB agar plate containing 50 μg/mL of ampicillin. The thus-obtained colonies were cultured in an LB liquid medium containing 50 μg/mL of ampicillin at 37° C. overnight, and the plasmid pBRgapP was collected from the thus-obtained bacterial cells.

To obtain the isopropyl alcohol dehydrogenase gene, amplification by PCR was carried out with AATATGCAT-GCTGGTGGAACATATGAAAGGTTTTG-CAATGCTAGG (SEQ ID NO: 11) and GCGGATCCGG-TACCTTATAATATAACTACTGCTTTAATTAAGTC (SEQ ID NO: 12) using the genomic DNA of *Clostridium beijerinckii* NRRL B-593 as a template. The thus-obtained DNA fragment was digested with the restriction enzymes SphI and BamHI to obtain an isopropyl alcohol dehydrogenase fragment having a size of about 1.1 kbp. The thus-obtained DNA fragment and a fragment obtained by digestion of the plasmid pBRgapP with the restriction enzymes SphI and BamHI were ligated using a ligase, and the *Escherichia coli* Strain DH5α competent cell (trade name: DNA-903, manufactured by Toyobo Co. Ltd.) was transformed with the resulting ligation product to obtain transformants growing on an LB agar plate containing 50 μg/mL of ampicillin. The obtained colonies were cultured in an LB liquid medium containing 50 μg/mL of ampicillin at 37° C. overnight, and the plasmid pGAP-IPAdh was collected from the thus-obtained bacterial cells.

To obtain the *Escherichia coli*-derived thiolase gene, amplification by PCR was carried out with ATGGATC-CGCTGGTGGAACATATGAAAAATTGTGT-CATCGTCAG (SEQ ID NO: 13) and GCAGAAGCT-TGTCTAGATTAATTCAACCGTTCAATCACCATC (SEQ ID NO: 14) using the genomic DNA of the *Escherichia coli* Strain MG1655 as the template. The thus-obtained DNA fragment was digested with the restriction enzymes BamHI and HindIII to obtain a thiolase fragment having a size of about 1.2 kbp. The thus-obtained DNA fragment and a fragment, which was obtained by digestion of the plasmid pGAP-IPAdh with the restriction enzymes BamHI and HindIII, were mixed and ligated using a ligase, and the *Escherichia coli* Strain DH5α competent cell (trade name: DNA-903, manufactured by Toyobo Co. Ltd.) were transformed with the resulting ligation product, to obtain transformants growing on an LB agar plate containing 50 μg/mL of ampicillin. The obtained colonies were cultured in an LB liquid medium containing 50 μg/mL of ampicillin at 37° C. overnight, and the plasmid pGAP-IPAdh-atoB was collected from the thus-obtained bacterial cells.

To obtain the *Escherichia coli*-derived CoA transferase gene, amplification by PCR was carried out with GCTCTA-GAGCTGGTGGAACATATGAAAACAAAAT-TGATGACATTACAAGAC (SEQ ID NO: 15) and TAG-CAAGCTTCTACTCGAGTTATTTGCTCTCCTGTGAAACG (SEQ ID NO: 16) using the genomic DNA of the *Escherichia coli* Strain MG1655 as the template. The thus-obtained DNA fragment was digested with the restriction enzymes XbaI and HindIII, to obtain a CoA transferase α subunit fragment having a size of about 600 bp. The thus-obtained DNA fragment and a fragment obtained by digestion of the plasmid pGAP-IPAdh-atoB with the restriction enzymes XbaI and HindIII, ligation was carried out using a ligase, and the *Escherichia coli* Strain DH5α competent cell (trade name: DNA-903, manufactured by Toyobo Co. Ltd.) was transformed with the resulting ligation product, to obtain transformants growing on an LB agar plate containing 50 μg/mL of ampicillin. The obtained colonies were cultured in an LB liquid medium containing 50 µg/mL of ampicillin at 37° C. overnight, and the plasmid pGAP-IPAdh-atoB-atoD was collected from the thus-obtained bacterial cells.

Further, amplification by PCR was carried out with AAGTCTCGAGCTGGTGGAACATATGGAT-GCGAAACAACGTATTG (SEQ ID NO: 17) and GGC-CAAGCTTCATAAATCACCCCGTTGC (SEQ ID NO: 18) using the genomic DNA of the *Escherichia coli* Strain MG1655 as the template, and the obtained DNA fragment was digested with the restriction enzymes XhoI and HindIII, to obtain a CoA transferase β subunit fragment having a size of about 600 bp. After mixing the obtained DNA fragment and fragments obtained by digestion of the plasmid pGAP-IPAdh-atoB-atoD with the restriction enzymes XhoI and HindIII, ligation was carried out using a ligase, and the *Escherichia coli* Strain DH5α competent cell (trade name: DNA-903, manufactured by Toyobo Co. Ltd.) was transformed with the resulting ligation product to obtain transformants growing on an LB agar plate containing 50 µg/mL of ampicillin. The thus-obtained colonies were cultured in an LB liquid medium containing 50 µg/mL of ampicillin at 37° C. overnight, and the plasmid pGAP-IPAdh-atoB-atoD-atoA was collected from the obtained bacterial cells.

To obtain the acetoacetate decarboxylase gene, amplification by PCR was carried out with CAGGTACCGCTGGTG-GAACATATGTTAAAGGATGAAGTAAT-TAAACAAATTAGC (SEQ ID NO: 19) and GCGGATCCTTACTTAAGATAAT-CATATATAACTTCAGC (SEQ ID NO: 20) using the genomic DNA of the *Clostridium acetobutylicum* ATCC824 as the template. The thus-obtained DNA fragment was digested with the restriction enzymes KpnI and BamHI to obtain an acetoacetate decarboxylase fragment having a size of about 700 bp. The thus-obtained DNA fragment and a fragment, which was obtained by digestion of the plasmid pGAP-IPAdh-atoB-atoD-atoA with the restriction enzymes KpnI and BamHI, were mixed and ligated using a ligase, and the *Escherichia coli* Strain DH5α competent cell (trade name: DNA-903, manufactured by Toyobo Co. Ltd.) was transformed with the resulting ligation product to obtain transformants growing on an LB agar plate containing 50 µg/mL of ampicillin. The obtained colonies were cultured in an LB liquid medium containing 50 µg/mL of ampicillin at 37° C. overnight, and the plasmid pGAP-Iaaa was collected from the obtained bacterial cells.

*Escherichia coli* strain B (ATCC11303) competent cell was transformed with this plasmid pGAP-Iaaa and cultured on an LB Broth Miller agar plate containing 50 µg/mL of ampicillin at 37° C. overnight to obtain *Escherichia coli* Strain pGAP-Iaaa/B.

The *Escherichia coli* Strain MG1655, *Clostridium acetobutylicum* ATCC824 and *Escherichia coli* strain B can be obtained from American Type Culture Collection, that is a bank of cells, microorganisms and genes.

Example 5

Production of Isopropyl Alcohol by *Escherichia Coli* Strain pGAP-Iaaa/B Using 1 L-Culture Vessel (1)

Production of isopropyl alcohol using a 1 L-culture vessel was studied in the same manner as in Example 3, except that in the preculturing, 25 mL of LB Broth Miller culture medium containing 0.1 g/L of ampicillin placed in an Erlenmeyer flask was used, and the *Escherichia coli* Strain pGAP-Iaaa/B obtained in Example 4 was inoculated thereto, followed by culturing for 16 hours at a culturing temperature of 35° C. with shaking at 120 rpm. The entire of the preculture medium was inoculated to a 1 L-culture vessel containing 475 mL of LB Broth Miller culture medium containing 50 g/L of glucose and one drop of decanal, and culturing was carried out. The culturing was carried out at a stirring rate of 500 rpm and a culturing temperature of 35° C., and pH of the culture medium was controlled to 7.0 using 24 wt/wt % sodium hydroxide solution. Samples were taken from the bacterial cell culture 24 hours after beginning of the culturing, and the bacterial cells were removed by centrifugation, followed by measurement of the accumulated amounts of isopropyl alcohol, butanol, and ethanol in the obtained culture supernatant according to a conventional method by HPLC. Accumulation of 5.5 g/L of isopropyl alcohol was confirmed after 24 hours of culturing. At this time, there was no accumulation of butanol and ethanol. The accumulated amount of isopropyl alcohol after 48 hours was 5.0 g/L. Each measured value is the sum of the content of isopropyl alcohol in the culture medium and that in the trap water (changed to 500 mL) after culturing.

Example 6

Production of Isopropyl Alcohol by *Escherichia Coli* Strain pGAP-Iaaa/B Using 1 L-Culture Vessel (2)

Production of isopropyl alcohol using a 1 L-culture vessel was studied in the same manner as in Example 5, except that in the culture in a 1 L-culture vessel, 475 mL of the culture medium with the composition indicated in Table 3 was used. The amount of the nitrogen atoms derived from ammonium sulfate at this time is 0.04% by mass based on the total mass of the culture medium at the beginning of the culture. Further, 50 wt/wt % aqueous glucose solution was added at a flow rate of 10 g/L/hour. As a result, accumulation of 7.4 g/L of isopropyl alcohol was confirmed after 24 hours of culturing. At this time, there was no accumulation of butanol and ethanol. The accumulated amount of isopropyl alcohol after 48 hours was 6.2 g/L. Each measured value is the sum of the content of isopropyl alcohol in the culture medium and that in the trap water (500 mL) after culturing.

TABLE 3

| Formulation of Medium | |
|---|---|
| Polypeptone | 2 g/L |
| $FeSO_4 \cdot 7H_2O$ | 0.09 g/L |
| $K_2HPO_4$ | 2 g/L |
| $KH_2PO_4$ | 2 g/L |
| $MgSO_4 \cdot 7H_2O$ | 2 g/L |
| $(NH_4)_2SO_4$ | 2 g/L |

(the remainder: water)

Example 7

Production of Isopropyl Alcohol by *Escherichia Coli* Strain pGAP-Iaaa/B Using 1 L-Culture Vessel (3)

Production of isopropyl alcohol using a 1 L-culture vessel was studied in the same manner as in Example 6, except that during the culture in a 1 L-culture vessel, 0.2% by mass (2 g/L) of $(NH_4)_2SO_4$ was added after 30 hours. The sum of the amount of the nitrogen atoms derived from ammonium sulfate in this Example is 0.08% by mass based on the total mass of the culture medium at the beginning of the culture. As a result, accumulation of 7.2 g/L of isopropyl alcohol was confirmed after 24 hours of culturing. At this time, there was no no accumulation of butanol and ethanol. The accumulated amount of isopropyl alcohol after 48 hours was 13.4 g/L. Each measured value is the sum of the content of isopropyl alcohol in the culture medium and that in the trap water (500 mL) after culturing. It was shown that addition of an appropriate amount of a nitrogen source such as ammonium sulfate increases the productivity.

Example 8

Production of Isopropyl Alcohol by *Escherichia Coli* Strain pGAP-Iaaa/B Using 1 L-Culture Vessel (4)

Production of isopropyl alcohol using a 1 L-culture vessel was studied in the same manner as in Example 6, except that in the formulation of the medium for the culture in a 1 L-culture vessel, the amount of $(NH_4)_2SO_4$ was changed to 0.4% by mass (4 g/L). The amount of the nitrogen atoms derived from ammonium sulfate in this Example is 0.08% by mass based on the total mass of the culture medium at the beginning of the culture. As a result, accumulation of 11.6 g/L of isopropyl alcohol was confirmed after 24 hours of culturing. The measured value is the sum of the content of isopropyl alcohol in the culture medium and that in the trap water (500 mL) after culturing. It was shown that addition of an appropriate amount of a nitrogen source such as ammonium sulfate increases the productivity.

Example 9

Production of Isopropyl Alcohol by *Escherichia Coli* Strain pGAP-Iaaa/B Using 1 L-Culture Vessel (5)

Production of isopropyl alcohol using a 1 L-culture vessel was studied in the same manner as in Example 6, except that in the formulation of the medium for the culture in a 1 L-culture vessel, the amount of $(NH_4)_2SO_4$ was changed to 0.5% by mass (5 g/L). The amount of the nitrogen atoms derived from ammonium sulfate in this Example is 0.11% by mass based on the total mass of the culture medium at the beginning of the culture. As a result, accumulation of 11.2 g/L of isopropyl alcohol was confirmed after 24 hours of culturing. Further, accumulation of 21.3 g/L of isopropyl alcohol was confirmed after 55 hours of culturing. The measured value is the sum of the content of isopropyl alcohol in the culture medium and that in the trap water (500 mL) after culturing.

Example 10

Production of Isopropyl Alcohol by *Escherichia Coli* Strain pGAP-Iaaa/B Using 1 L-Culture Vessel (6)

Production of isopropyl alcohol using a 1 L-culture vessel was studied in the same manner as in Example 6, except that 12.5% by mass-aqueous ammonia solution was used as a pH adjuster. As a result, accumulation of 13.3 g/L of isopropyl alcohol was confirmed after 24 hours of culturing. Further, accumulation of 28.4 g/L of isopropyl alcohol was confirmed after 55 hours of culturing. The mass of the 12.5% by mass-aqueous ammonia solution added by 55 hours was 69.0 g, and the sum of the amount of the nitrogen atoms derived from the aqueous ammonia solution is 0.73% by mass based on the total mass of the culture medium at the beginning of the culture. The measured value is the sum of the content of isopropyl alcohol in the culture medium and that in the trap water (500 mL) after culturing.

Example 11

Production of Isopropyl Alcohol by *Escherichia Coli* Strain pGAP-Iaaa/B Using 1 L-Culture Vessel (7)

Production of isopropyl alcohol using a 1 L-culture vessel was studied in the same manner as in Example 6, except that in the formulation of the medium for the culture in a 1 L-culture vessel, 2 g/L of polypeptone was replaced with 20 g/L of corn steep liquor (manufactured by Nihon Shokuhin Kako Co., Ltd.), and the amount of $(NH_4)_2SO_4$ was changed to 5 g/L. As a result, accumulation of 10.9 g/L of isopropyl alcohol was confirmed after 24 hours of culturing. Further, accumulation of 17.8 g/L of isopropyl alcohol was confirmed after 55 hours of culturing. The sum of the amount of the nitrogen atoms derived from ammonium sulfate in this Example is 0.11% by mass based on the total mass of the culture medium at the beginning of the culture. The measured value is the sum of the content of isopropyl alcohol in the culture medium and that in the trap water (500 mL) after culturing. It was shown that a wide variety of components can be used as nutrient sources for the medium.

Example 12

Production of Isopropyl Alcohol by *Escherichia Coli* strain pIPA/B Using 1 L-Culture Vessel (2)

Culturing for Isopropyl alcohol using a 1 L-culture vessel was studied in the same manner as in Example 3, except that at the beginning of the culture, 0.5% (5 g/L) of $(NH_4)_2SO_4$ was added. The amount of the nitrogen atoms derived from ammonium sulfate in this Example is 0.11% by mass based on the total mass of the culture medium at the beginning of the culture. As a result, accumulation of 4.5 g/L of isopropyl alcohol was confirmed after 48 hours of culturing.

Example 13

Collection of Isopropyl Alcohol from Culture Medium by Distillation Method

The strain pIPA/B was cultured according to the method in Example 3 to obtain 180 g of a culture medium to be subjected to distillation. This is referred to as a culture medium A. 178.6 g of the culture medium A was placed in a collection flask having a capacity of 200 mL and heated while being agitated in an oil bath to carry out simple distillation according to a conventional method. The overhead temperature and liquid amount of the culture medium A in each step are shown in Table 4. The contents of isopropyl alcohol, butanol and ethanol contained in the culture medium before distillation as well as in aliquots of the liquid collected by distillation and in the residual liquid were measured according to a conventional method by HPLC. The results are shown in Table 5. From the culture medium obtained by culturing the strain pIPA/B of this Example, almost all of the contained isopropyl alcohol could be collected with an overhead temperature of 99.1° C. to 99.5° C. At this time, butanol and ethanol were not detected in the collected aliquots.

Comparative Example 1

Similarly to the composition of the culture medium for the *Clostridium* sp. 172CY-02 strain described in JP-A No. 61-67493, 180 g of a culture medium having 9.9 g/L of n-butanol, 0.6 g/L of ethanol and 7.2 g/L of isopropyl alcohol added to LB Broth Miller culture medium was prepared, which culture medium was referred to as a comparative culture medium B. 177.9 g of the comparative culture medium B was placed in a recovery flask having a capacity of 200 mL and heated while being agitated in an oil bath, to carry out simple distillation according to a conventional method. The overhead temperature and liquid amount of the comparative culture medium B in each step are shown in Table 4. The contents of isopropyl alcohol, butanol and ethanol contained in the liquid before distillation as well as in aliquots of the liquid collected by distillation and in the residual liquid were measured according to a conventional method by HPLC. The results are shown in Table 5. It is remarked that among the three kinds of the mixed alcohol components in the comparative culture medium B, isopropyl alcohol and butanol showed the same distillation behavior, so that isopropyl alcohol could not be separated and collected solely.

Based on the results in Example 13 and Comparative example 1, it is understood that isopropyl alcohol can be easily collected from the culture medium of the invention since it does not contain alcohols other than isopropyl alcohol as by-products. Thus, isopropyl alcohol can be collected from the culture medium according to the invention by a simple purification process such as simple distillation.

On the other hand, it was understood that collection of isopropyl alcohol from culture media processed with existing bacteria is not simple because separation of isopropyl alcohol from by-product alcohols is difficult. Collection of isopropyl alcohol from a culture medium processed with an existing bacterium is expected to require distillation using incidental facilities such as a rectifying column, so that the purification process is expected to be complicated.

In consideration of these, the isopropyl alcohol-producing bacteria of the invention may be superior to those in the prior art with respect to practical applications of production of plant-derived isopropyl alcohol.

TABLE 4

Overhead Temperatures and Liquid Amounts of Culture Medium A and Comparative Culture Medium B

| Distillation step | Culture medium A | | Comparative culture medium B | |
|---|---|---|---|---|
| | Overhead temperature (° C.) | Liquid amount (g) | Overhead temperature (° C.) | Liquid amount (g) |
| Fraction 1 | 99.1-99.5 | 10.1 | 96.0-98.0 | 9.4 |
| Fraction 2 | 99.5 | 10.0 | 99.4 | 9.6 |
| Fraction 3 | 99.8 | 11.0 | 99.5 | 10.4 |
| Fraction 4 | 99.8 | 20.6 | 99.5 | 20.3 |
| Fraction 5 | 99.8 | 21.9 | 99.9 | 18.8 |
| Residual liquid after distillation | | 100.9 | | 107.5 |

TABLE 5

Results of Measurement by HPLC

| | | Isopropyl alcohol (g) | Butanol (g) | Ethanol (g) |
|---|---|---|---|---|
| Culture medium A | Before distillation | 0.48 | 0.00 | 0.00 |
| | Fraction 1 | 0.43 | 0.00 | 0.00 |
| | Fraction 2 | 0.02 | 0.00 | 0.00 |
| | Fraction 3 | 0.00 | 0.00 | 0.00 |
| | Fraction 4 | 0.00 | 0.00 | 0.00 |
| | Fraction 5 | 0.00 | 0.00 | 0.00 |
| | Residual liquid | 0.00 | 0.00 | 0.00 |
| Comparative culture medium B | Before distillation | 1.20 | 1.69 | 0.10 |
| | Fraction 1 | 0.93 | 1.35 | 0.06 |
| | Fraction 2 | 0.22 | 0.30 | 0.03 |
| | Fraction 3 | 0.01 | 0.02 | 0.01 |
| | Fraction 4 | 0.00 | 0.00 | 0.00 |
| | Fraction 5 | 0.00 | 0.00 | 0.00 |
| | Residual liquid | 0.00 | 0.00 | 0.00 |

Example 14

Test Example

Processing in this Example was carried out using the production apparatus 10 shown in FIG. 1. The culture vessel 12 had a capacity of 1 L, and the trap vessel 40 had a capacity of 500 mL. All of the culture vessel 12, trap vessel 40, injection duct 16, connecting duct 30 and exhaust duct 44 were made of glass, 400 mL of water (trap water) as the trap liquid 42 was injected into the trap vessel 40.

10 g/L aqueous isopropyl alcohol solution was injected to the 500 mL culture vessel 12 as the processing liquid. The processing was carried out at a stirring rate of 500 rpm and a processing temperature of 37° C.

Air was subsequently introduced from the ion duct 16 into the aqueous isopropyl alcohol solution at a rate of 0.5 L/min. (1 vvm) and the processing was started. The exhaust from the culture vessel 12 was bubbled into the trap liquid 42 in the trap vessel 40. The exhaust from the trap vessel 40 was released to the atmosphere outside the apparatus system. Each of the processing liquid in the culture vessel 12 and the trap liquid 42 in the trap vessel 40 was sampled 0, 2, 4, 8 and 24 hours after the beginning of the processing, and the accumulated amount of isopropyl alcohol in each sample was measured by HPLC. The measurement by HPLC was carried out with ULTRON PS-80H (trade name, manufactured by Shinwa Chemical Industries Ltd.; ID: 8.0 mm, L: 300 mm) using 0.1% $HClO_4$ as an eluent, at a flow rate of 1.0 mL/min., and a column temperature of 50° C., and using a differential refractive index detector (RI) as a detector. The results are shown in Table 6.

TABLE 6

| Processing time (Hrs.) | Accumulated amount of Isopropyl alcohol (g/L) | | |
|---|---|---|---|
| | Processing liquid | Trap water | Total amount |
| 0 | 10.1 | 0.0 | 10.1 |
| 2 | 9.8 | 1.2 | 11.0 |
| 4 | 8.5 | 2.4 | 10.9 |
| 8 | 7.1 | 3.8 | 10.9 |
| 24 | 3.1 | 7.0 | 10.1 |

As shown in Table 6, the concentration of isopropyl alcohol in the culture vessel 12 decreased over time, and the isopropyl alcohol concentration in the trap liquid 42 gradually increased. It was revealed that 70% of isopropyl alcohol in the culture vessel had moved to the water bottle when 24 hours passed. At this time, the total amount of isopropyl alcohol was 10.1 g, and the material balance was almost consistent therewith.

Therefore, it was revealed that, by bubbling the exhaust from the aeration culture in the culture vessel 12 into the trap liquid 42 in the trap vessel 40, isopropyl alcohol in the processing liquid can be separated from the processing liquid and dissolved into the trap liquid 42.

Example 15

Production of Isopropyl Alcohol

In this Example, isopropyl alcohol was produced using the production apparatus 10, which is the same as that used in Example 3. The trap vessel 40 contained water (trap water) as the trap liquid 42 injected at an amount of 400 mL.

As preculturing, 4 mL of LB Broth Miller culture medium containing 0.1 g/L of ampicillin and 2 g/L of glucose was placed in a test tube having a diameter of 19 mm and length of 175 mm, and the strain pIPA/B obtained in Example 1 was inoculated thereto, followed by culturing at a culturing temperature of 37° C. with shaking at 120 rpm for 18 hours.

The preculture medium was inoculated to the culture vessel 12 containing 500 mL of LB Broth Miller culture medium containing 0.1 g/L of ampicillin, 20 g/L of glucose and one drop of decanal, and culturing was started. The culturing was carried out at a stirring rate of 500 rpm and a culturing temperature of 37° C., and pH of the culture medium was adjusted to 7.0 using 12.5%-aqueous ammonia solution.

Subsequently, aeration culture was started by injecting the air from the injection duct 16 into the culture medium at a rate of 0.5 L/min. (1 vvm). The exhaust from the culture vessel 12 was bubbled into the trap liquid 42 in the trap vessel 40.

At the time when 23 hours have passed from the beginning of the culture, 20 mL of 0.5 g/L glucose solution was added to the culture vessel.

Detection of Isopropyl Alcohol in Samples

The bacterial cell culture medium in the culture vessel 12 after the processing and the trap liquid 42 in the trap vessel 40 after the processing were sampled 0, 7, 23, 30, 47 and 52 hours after the beginning of the culture. Each sampled culture medium was subjected to centrifugation to remove solids such as bacterial cells in the culture medium.

The accumulated amount of isopropyl alcohol in each of the sampled culture medium and water was measured by HPLC. The results are shown in Table 7.

Further, with respect to the culture medium and trap water obtained 47 hours after the beginning of the culture, the number of peaks, Rt times (Retention times) and the names of compounds detected by subjecting the culture medium to measurement by HPLC are shown in Table 8, and those detected by subjecting the trap water to measurement by HPLC are shown in Table 9.

In Tables 8 and 9, "IPA" indicates isopropyl alcohol. In Table 8, the compound names indicated as "Unknown" are assumed to be impurities generated by the aeration culture of isopropyl alcohol.

TABLE 7

| Culturing time (Hrs.) | In culture medium (g/L) | In water (g/L) |
| --- | --- | --- |
| 0 | 0.0 | 0.0 |
| 7 | 0.0 | 0.0 |
| 23 | 0.8 | 0.3 |
| 30 | 1.3 | 0.7 |
| 47 | 1.4 | 1.7 |
| 52 | 1.0 | 2.0 |

TABLE 8

| Peak No. | Rt (min.) | Compound name |
| --- | --- | --- |
| 1 | 5.15 | Unknown |
| 2 | 6.24 | Unknown |
| 3 | 6.7 | Unknown |
| 4 | 7.33 | Glucose |
| 5 | 7.98 | Unknown |
| 6 | 8.89 | Unknown |
| 7 | 9.52 | Unknown |
| 8 | 10.19 | Unknown |
| 9 | 11.91 | Acetic acid |
| 10 | 14.07 | Unknown |
| 11 | 17.42 | Unknown |
| 12 | 18.77 | IPA |

TABLE 9

| Peak No. | Rt (min.) | Compound name |
| --- | --- | --- |
| 1 | 18.76 | IPA |

As shown in Table 7 to Table 9, it is confirmed that isopropyl alcohol produced using the isopropyl alcohol-producing bacteria is accumulated in the culture medium and trap water by the aeration culture.

11 peaks assumed to be derived from impurities in addition to glucose and acetic acid were found from the culture medium obtained 47 hours after the beginning of the culture, but there was no peak other than the one corresponding to isopropyl alcohol was found from the trap water at this time. Thus, it is revealed that, according to this production method, impurities and isopropyl alcohol can be easily separated from each other by bubbling the exhaust from the culture vessel 12 into the trap liquid 42.

Thereby, isopropyl alcohol can be collected efficiently by performing simple operations in the steps from the beginning of the culture to the collection of isopropyl alcohol. Further, it is revealed that an aqueous isopropyl alcohol solution having no impurities can be obtained by using water for collection of isopropyl alcohol. The invention can therefore be said to be a groundbreaking method in the practical implementation of isopropyl alcohol production through culturing microorganisms, the method thereof allowing construction of a production process with a reduced burden in purifying.

Comparative Example 2

Construction of pIPA Plasmid Lacking Thiolase Gene and Construction of Transformant with the Plasmid A plasmid pIPAΔthio, that has a structure of the plasmid pIPA described in Example 1 with removing the thiolase gene therefrom, was prepared.

To isolate the thiolase promoter from pIPA, amplification by PCR was carried out with TTT GAA TTC CAT GAT TTT AAG GGG GTT AGC ATA TGC A (SEQ ID NO:21) and TTT TCT AGA TCT AAC TAA CCT CCT AAA TTT TGA TAC GGG (SEQ ID NO:22) using pIPA as the template, and the thus-obtained DNA fragment was digested with the restriction enzymes EcoRI and KpnI to obtain a thiolase promoter fragment having a size of about 240 bp.

To isolate the isopropyl alcohol dehydrogenase gene from pIPA, amplification by PCR was carried out with TTT CTC GAG GCA GAT TTT GCT ACT CTT GGA GC (SEQ ID NO:23) and TTT GGT ACC GCA GAT TTT GCT ACT CTT GGA GC (SEQ ID NO:24) using pIPA as the template, and the obtained DNA fragment was digested with the restriction enzymes EcoRI and XbaI to obtain a isopropyl alcohol dehydrogenase gene fragment having a size of about 1.4 kbp.

The above-described two DNA fragments and 4.9 kbp a fragment obtained by digesting the plasmid pIPA with the restriction enzymes EcoRI and KpnI were mixed and ligated using a ligase, and *Escherichia coli* Strain DH5α competent cell (trade name: DNA-903, manufactured by Toyobo Co. Ltd.) were transformed with the resulting ligation product to obtain transformants growing on an LB agar plate containing 100 μg/mL of ampicillin. The thus-obtained colonies were cultured in an LB liquid medium containing 100 μg/mL of ampicillin at 37° C. overnight, and the plasmid pIPAΔthio was collected from the obtained bacterial cells. The base sequence of pIPAΔthio was determined by a conventional method, and the DNA sequences of the thiolase promoter and isopropyl alcohol dehydrogenase gene were confirmed as including no error.

*Escherichia coli* strain B (ATCC11303) competent cell was transformed with this plasmid pIPAΔthio, and cultured on an LB Broth Miller agar plate containing 100 μg/mL of ampicillin at 37° C. overnight to obtain the transformant strain pIPAΔthio/B.

Production of Isopropyl Alcohol by *Escherichia Coli* Strain pIPAΔthio/B Using 1 L-Culture Vessel A production test of isopropyl alcohol using a 1 L-culture vessel was carried out in the same manner as in Example 3. As preculturing, 4 mL of LB Broth Miller culture medium containing 0.1 g/L of ampicillin and 2 g/L of glucose was placed in a test tube, and the *Escherichia coli* strain pIPAΔthio/B was inoculated thereto, followed by culturing for 18 hours at a culturing temperature of 37° C. with shaking at 120 rpm. The entire of the preculture medium was inoculated to a 1 L-culture vessel containing 500 mL of LB Broth Miller culture medium containing 20 g/L of glucose and one drop of decanal, and culturing was carried out. The culturing was carried out at a stirring rate of 500 rpm and a culturing temperature of 37° C., and pH of the culture medium was controlled to 7.0 using 12.5%-ammonia solution. 20 mL of glucose at a concentration of 0.5 g/mL was further added to the culture by 72 hours after the beginning of the culturing. Samples were taken from the bacterial cell culture with time lapse from the beginning of the culture, and the bacterial cells were removed by centrifugation, followed by measurement of the accumulated amount of isopropyl alcohol in the obtained culture supernatant according to a conventional method by HPLC. The results are shown in Table 10. Each measured value in Table 10 is the sum of the content of isopropyl alcohol in the culture medium and that in the trap water after culturing.

Each of the acetoacetate decarboxylase, isopropyl alcohol dehydrogenase and CoA transferase genes is introduced, but the thiolase gene is not introduced in the *Escherichia coli* strain pIPAΔthio/B. Therefore, the activity of the thiolase of this strain is inherent one thereof. However, there was no accumulation of isopropyl alcohol even after 72 hours of culturing of the *Escherichia coli* strain pIPAΔthio/B.

TABLE 10

| Results of Measurement by HPLC | |
| --- | --- |
| Culturing time | Isopropyl alcohol |
| 0 | 0.0 g/L |
| 9 | 0.0 g/L |
| 24 | 0.0 g/L |
| 30 | 0.0 g/L |
| 48 | 0.0 g/L |

TABLE 10-continued

| Results of Measurement by HPLC | |
| --- | --- |
| Culturing time | Isopropyl alcohol |
| 54 | 0.0 g/L |
| 72 | 0.0 g/L |

Comparative Example 3

Construction of pIPA Plasmid Lacking Thiolase Gene and CoA Transferase, and Construction of Transformant with the Plasmid A plasmid pIPAΔthioΔctfAB, that has a structure of the plasmid pIPA described in Example 1 with removing the thiolase gene and CoA transferase therefrom, was prepared.

The pIPAΔthio was digested with the restriction enzymes KpnI and BamHI, and the terminals of the DNA were blunted and ligated to each other, followed by transformation of *Escherichia coli* Strain DH5α competent cell (trade name: DNA-903, manufactured by Toyobo Co. Ltd.) with the plasmid to obtain transformants growing on an LB agar plate containing 100 μg/mL of ampicillin. The thus-obtained colonies were cultured in an LB liquid medium containing 100 μg/mL of ampicillin at 37° C. overnight, and the plasmid pIPAΔthioΔctfAB was collected from the obtained bacterial cells.

The transformant strain pIPAΔthioΔctfAB/B was obtained by transforming *Escherichia coli* strain B (ATCC11303) competent cell with the plasmid pIPAΔthioΔctfAB, followed by culturing thereof on an LB Broth Miller culture medium (Difco244620) agar plate containing 100 μg/mL of ampicillin at 37° C. overnight.

Production of Isopropyl Alcohol by *Escherichia Coli* Strain pIPAΔthioΔctfAB/B Using 1 L-Culture Vessel Production of isopropyl alcohol using a 1 L-culture vessel was studied in the same manner as in Example 3, except that in the preculturing, 4 mL of LB Broth Miller culture medium containing 0.1 g/L of ampicillin and 2 g/L of glucose was placed in a test tube, and the *Escherichia coli* strain pIPAΔthioΔctfAB/B was inoculated thereto, followed by culturing for 18 hours at a culturing temperature of 37° C. with shaking at 120 rpm. The entire of the preculture medium was inoculated to a 1 L-culture vessel containing 500 mL of LB Broth Miller culture medium containing 20 g/L of glucose and one drop of decanal, and culturing was carried out. The culturing was carried out at a stirring rate of 500 rpm and a culturing temperature of 37° C., and pH of the culture medium was controlled to 7.0 using 12.5%-ammonia solution. Further, 20 mL of glucose at a concentration of 0.5 g/mL was added to the culture by 72 hours after the beginning of the culture.

The bacterial cell culture medium was sampled with time lapse from the beginning of the culture, and the bacterial cells were removed by centrifugation, followed by measurement of the accumulated amount of isopropyl alcohol in the thus-obtained culture supernatant according to a conventional method by HPLC. The results are shown in Table 11. The amount of isopropyl alcohol in Table 11 is the sum of the content of isopropyl alcohol in the culture medium and that in the trap water after culturing.

The genes for acetoacetate decarboxylase and isopropyl alcohol dehydrogenase are introduced, but the thiolase gene and CoA transferase gene are not introduced in the *Escherichia coli* strain pIPAΔthioΔctfAB/B. Therefore, the activities of the thiolase gene and CoA transferase gene of this strain are inherent one thereof. However, there was no accumulation of isopropyl alcohol even after 72 hours of culturing of the *Escherichia coli* strain pIPAΔthioΔctfAB/B.

TABLE 11

Results of Measurement by HPLC

| Culturing time | Isopropyl alcohol |
|---|---|
| 0 | 0.0 g/L |
| 9 | 0.0 g/L |
| 24 | 0.0 g/L |
| 30 | 0.0 g/L |
| 48 | 0.0 g/L |
| 54 | 0.0 g/L |
| 72 | 0.0 g/L |

From the results in Examples 1, 2 and 3 and Comparative examples 2 and 3, it can be seen that *E. coli* obtained according to the invention produce no isopropyl alcohol when it fails to be provided thereto the activities of thiolase and CoA transferase encoded by genes for these enzymes, which inherently exist in the genome of *E. coli*, in addition to the activities of acetoacetate decarboxylase and isopropyl alcohol dehydrogenase.

Example 16

Construction of Vector for Expression of Thiolase Gene Derived from *Escherichia Coli*, CoA Transferase Gene derived from *Escherichia coli*, Acetoacetate Decarboxylase Gene Derived from Bacterium of Genus *Clostridium* and Isopropyl Alcohol Dehydrogenase Gene Derived from Bacterium of Genus *Clostridium* Using glyA Promoter and Transformant with the Expression Vector The promoter for the serine hydroxymethyltransferase gene (glyA) derived from *Escherichia coli* was herein used instead of the GAPDH promoter in Example 4.

The amino acid sequence of serine hydroxymethyltransferase of *Escherichia coli* and the base sequence of the gene thereof have been already reported. That is, the gene encoding serine hydroxymethyltransferase is described in GenBank accession number V00283. The genes required for production of isopropyl alcohol can be expressed using its promoter.

To obtain the glyA promoter, amplification by PCR was carried out with TCGACCGGCTCCAGTTCG (SEQ ID NO: 25) and CTGTCGCATGCTGACTCAGCTAA-CAATAAAATTTTTGG (SEQ ID NO: 26) using the genomic DNA of *Escherichia coli* Strain MG1655 as the template, and the obtained DNA fragment was digested with the restriction enzyme SPhI to obtain a DNA fragment having a size of about 850 by corresponding to the glyA promoter. The thus-obtained DNA fragment and fragments obtained by treatment of the plasmid pBR322 (GenBank accession number J01749) with the restriction enzyme NdeI and subsequent blunting with T4 DNA polymerase treatment followed by digestion with SphI were mixed and ligated using a ligase, and *Escherichia coli* Strain DH5α competent cell (trade name: DNA-903, manufactured by Toyobo Co. Ltd.) was transformed with the resulting ligation product, to obtain transformants growing on an LB agar plate containing 50 μg/mL of ampicillin. The thus-obtained colonies were cultured in an LB liquid medium containing 50 μg/mL of ampicillin at 37° C. overnight, and the plasmid pBRglyP was collected from the thus-obtained bacterial cells.

Thereafter, in the same manner as in Example 4, the genes encoding each of thiolase, CoA transferase, isopropyl alcohol dehydrogenase and acetoacetate decarboxylase were sequentially introduced, and the plasmid pGly-Iaaa was collected.

*Escherichia coli* strain pGly-Iaaa/B was obtained by transforming the *Escherichia coli* strain B (ATCC11303) competent cells with this plasmid pGly-Iaaa, followed by culturing thereof on an LB Broth Miller agar plate containing 50 μg/mL of ampicillin at 37° C. overnight.

Example 17

Construction of Vector for Expression of Thiolase Gene Derived from *Escherichia Coli*, CoA Transferase Gene Derived from *Escherichia coli*, Acetoacetate Decarboxylase Gene Derived from Bacterium of Genus *Clostridium* and Isopropyl Alcohol Dehydrogenase Gene Derived from Bacterium of Genus *Clostridium* Using gadA Promoter and Transformant with the Expression Vector The promoter for the glutamate decarboxylase A gene (gadA) derived from *Escherichia coli* was herein used instead of the GAPDH promoter in Example 4.

The amino acid sequence of glutamate decarboxylase A of *Escherichia coli* and the base sequence of the gene thereof have been already reported. That is, the gene encoding glutamate decarboxylase A is described in GenBank accession number M84024. The genes required for production of isopropyl alcohol can be expressed using its promoter.

To obtain the gadA promoter, amplification by PCR was carried out with CGACTCGCATATGTCGTTTTTCTGCT-TAGG (SEQ ID NO: 27) and CAGTCGCATGCTTC-GAACTCCTTAAATTTATTTGAAGGC (SEQ ID NO: 28) using the genomic DNA of the *Escherichia coli* Strain MG1655 as the template, and the obtained DNA fragment was digested with the restriction enzymes NdeI and SphI to obtain a DNA fragment having a size of about 130 by corresponding to the gadA promoter. The thus-obtained fragment and a fragment obtained by digesting the plasmid pBR322 (GenBank accession number J01749) with the restriction enzymes NdeI and SphI were mixed and ligated using a ligase, and *Escherichia coli* Strain DH5α competent cell (trade name: DNA-903, manufactured by Toyobo Co. Ltd.) was transformed with the resulting ligation product to obtain transformants growing on an LB agar plate containing 50 μg/mL of ampicillin. The thus-obtained colonies were cultured in an LB liquid medium containing 50 μg/mL of ampicillin at 37° C. overnight, and the plasmid pBRgadP was collected from the thus-obtained bacterial cells.

Thereafter, in the same manner as in Example 4, the genes encoding each of thiolase, CoA transferase, isopropyl alcohol dehydrogenase and acetoacetate decarboxylase were sequentially introduced, and the plasmid pGad-Iaaa was collected.

By transformation of the *Escherichia coli* strain B (ATCC11303) competent cells with this plasmid pGad-Iaaa, followed by culturing thereof on an LB Broth Miller agar plate containing 50 μg/mL of ampicillin at 37° C. overnight, the *Escherichia coli* strain pGad-Iaaa/B was obtained.

Example 18

Production of Isopropyl Alcohol by *Escherichia coli* Strain pGly-Iaaa/B and Strain pGad-Iaaa/B Using 1 L-Culture Vessel Production of isopropyl alcohol by the *Escherichia coli* strain pGly-Iaaa/B and strain pGad-Iaaa/B using a 1 L-culture vessel was studied in the same manner as in Example 5. As a result, after 24 hours of culturing, accumulation of isopropyl alcohol at a concentration of 3.1 g/L by the strain pGly-Iaaa/B and that at a concentration of 2.6 g/L by the strain pGad-Iaaa/B were confirmed. Each measured value is the sum of the content of isopropyl alcohol in the culture medium and that in the trap water (500 mL) after culturing.

Example 19

Isopropyl Alcohol Productivity in Culturing Strain pGAP-Iaaa/B at Aeration volume of 1 vvm or 2 vvm In this Example, isopropyl alcohol was produced using two apparatuses, each of which is the same as the apparatus 10 used in Example 5 except the capacity of the trap vessel. Each of the trap vessels 40 herein had a capacity of 2000 mL and contained water (trap water) as the trap liquid 42 at a volume of 2000 mL.

As preculturing, 25 mL of LB Broth Miller culture medium containing 0.1 g/L of ampicillin placed in an Erlenmeyer flask was used, and the *Escherichia coli* Strain pGAP-Iaaa/B was inoculated thereto, followed by culturing for 16 hours at a culturing temperature of 35° C. with shaking at 120 rpm. The entire of the preculture medium was inoculated to a 1 L-culture vessel containing 475 mL of LB Broth Miller culture medium containing 50 g/L of glucose and one drop of decanal, and culturing was carried out. The culturing was carried out at a stirring rate of 500 rpm and a culturing temperature of 35° C., and pH of the culture medium was adjusted to 7.0 using NaOH.

Subsequently, in one of the production apparatuses, aeration culture was started by injecting the air from the injection duct 16 into the culture medium such that 1 vvm is attained. In the other production apparatus, two injection ducts 16 were used, and aeration culture was started by injecting the air and nitrogen gas such that 1 vvm for each gas is attained to have for the total aeration volume be 2 vvm. The exhaust from the culture vessel 12 was bubbled into the trap liquid in the trap vessel 40.

As a result, after 24 hours of culturing, accumulation of isopropyl alcohol at a concentration of 5.5 g/L by the sample with the aeration volume of 1 vvm and that at a concentration of 3.3 g/L by the sample with 2 vvm were confirmed. Each measured value is the sum of the content of isopropyl alcohol in the culture medium and that in the trap water after culturing. The amount of isopropyl alcohol in the trap water was calculated by multiplying the isopropyl alcohol concentration in the water by 4 to convert the value into the corresponding amount in the culture medium.

Example 20

Isopropyl Alcohol Productivity in Culturing Strain pIPA/B at Aeration volume of 1 vvm or 0.75 vvm Culturing of the strain pIPA/B was studied in the same manner as in Example 3, except that the glucose concentration was changed to 40 g/L, and an aqueous ammonia solution was used as the pH adjuster. Each trap vessel 40 had a capacity of 500 mL, and contained water (trap water) as the trap liquid 42 at an amount of 500 mL. The air was used as an aeration gas, and the aeration volume thereof was adjusted to 1 vvm or 0.75 vvm. As a result, after 54 hours of culturing, accumulation of isopropyl alcohol at a concentration of 2.8 g/L by the sample with the aeration volume of 1 vvm and that at a concentration of 2.8 g/L by the sample with the aeration volume of 0.75 vvm were confirmed. Each measured value is the sum of the content of isopropyl alcohol in the culture medium and that in the trap water after culturing.

From the results in Examples 19 and 20, the present inventors found that an aeration volume can be optimized for production of isopropyl alcohol. We found that the total aeration volume injected to the culture vessel can be preferably 0.75 to 1 vvm comparing to 2 wm for production of isopropyl alcohol.

Thus, according to embodiments of the invention, less by-product alcohols are generated, and isopropyl alcohol which is more highly purified can be conveniently and efficiently produced only by simple purification without requiring a step for separating by-product alcohols.

Isopropyl alcohol obtained by the invention can be applied for various uses. For example, it can be preferably used as a raw material for production of propylene.

The disclosure of Japanese Patent Application No. 2007-181571 is hereby incorporated by reference in its entirety.

All the literatures, patent applications and technical standards described in the present specification are incorporated into the present specification by reference, to the same extent as in cases where the individual literatures, patent applications and technical standards are concretely and individually described to be incorporated by reference.

The invention claimed is:

1. An isopropyl alcohol-producing *E. coli* comprising:
a gene encoding active acetoacetate decarboxylase of the genus *Clostridium*,
a gene encoding active isopropyl alcohol dehydrogenase of the genus *Clostridium*,
a gene encoding active CoA transferase of the genus *Clostridium* or genus *Escherichia*, and
a gene encoding active thiolase of the genus *Clostridium* or genus *Escherichia*,
wherein the gene encoding active acetoacetate decarboxylase of the genus *Clostridium*, the gene encoding active isopropyl alcohol dehydrogenase of the genus *Clostridium*, the gene encoding active CoA transferase of the genus *Clostridium* or genus *Escherichia* and the gene encoding active thiolase of the genus *Clostridium* or genus *Escherichia* are linked operably to a glyceraldehyde-3-phosphate dehydrogenase (GAPDH) promoter,
and wherein the *E. coli* is capable of producing isopropyl alcohol from a plant-derived material.

2. The *E. coli* according to claim 1, wherein the gene encoding active CoA transferase of the genus *Clostridium* or genus *Escherichia* is a gene encoding active CoA transferase of the genus *Escherichia*, and the gene encoding active thiolase of the genus *Clostridium* or genus *Escherichia* is a gene encoding active thiolase of the genus *Escherichia*.

3. The *E. coli* according to claim 1, wherein the gene encoding active CoA transferase of the genus *Clostridium* or genus *Escherichia* is a gene encoding active CoA transferase of the genus *Clostridium*, and the gene encoding active thiolase of the genus *Clostridium* or genus *Escherichia* is a gene encoding active thiolase of the genus *Clostridium*.

4. The *E. coli* according to claim 2, wherein:
(a) the gene encoding active acetoacetate decarboxylase of the genus *Clostridium* is a gene encoding active acetoacetate decarboxylase of *Clostridium acetobutylicum*;
(b) the gene encoding active isopropyl alcohol dehydrogenase of the genus *Clostridium* is a gene encoding active isopropyl alcohol dehydrogenase of *Clostridium beijerinckii*, (c) the gene encoding active CoA transferase of the genus *Escherichia* is a gene encoding active CoA transferase of *Escherichia coli*; and
(d) the gene encoding active thiolase of the genus *Escherichia* is a gene encoding active thiolase of *Escherichia coli*.

5. The *E. coli* according to claim 3, wherein:
(a) the gene encoding active acetoacetate decarboxylase of the genus *Clostridium* is a gene encoding active acetoacetate decarboxylase of *Clostridium acetobutylicum*;
(b) the gene encoding active isopropyl alcohol dehydrogenase of the genus *Clostridium* is a gene encoding active isopropyl alcohol dehydrogenase of *Clostridium beijerinckii*,
(e) the gene encoding active CoA transferase of the genus *Clostridium* is a gene encoding active CoA transferase of *Clostridium acetobutylicum*; and
(f) the gene encoding active thiolase of the genus *Clostridium* is a gene encoding active thiolase of *Clostridium acetobutylicum*.

6. The *E. coli* according to claim 4, wherein:
(a) the gene encoding active acetoacetate decarboxylase of *Clostridium acetobutylicum* is isolated by primers consisting of SEQ ID NO:19 and SEQ ID NO:20;
(b) the gene encoding active isopropyl alcohol dehydrogenase of *Clostridium beijerinckii* is isolated by primers consisting of SEQ IDS NO:11 and SEQ ID NO:12;
(c) the gene encoding active CoA transferase of *Escherichia coli* is isolated by primers consisting of SEQ ID N0:15, SEQ ID NO:16, SEQ ID NO:17 and SEQ ID NO:18; and
(d) the gene encoding active thiolase of *Escherichia coli* is isolated by primers consisting of SEQ ID NO:13 and SEQ ID NO:14.

7. The *E. coli* according to claim 5, wherein:
(a) the gene encoding active acetoacetate decarboxylase of *Clostridium acetobutylicum* is isolated by primers consisting of SEQ ID NO:5 and SEQ ID NO:6;
(b) the gene encoding active isopropyl alcohol dehydrogenase of *Clostridium beijerinckii* is isolated by primers consisting of SEQ ID NO:7 and SEQ ID NO:8;

(e) the gene encoding active CoA transferase of *Clostridium acetobutylicum* is isolated by primers consisting of SEQ ID NO:3 and SEQ ID NO:4; and (f) the gene encoding active thiolase of *Clostridium acetobutylicum* is isolated by primers consisting of SEQ ID NO:1 and SEQ ID NO:2.

8. The E. coli according to claim 4, wherein the *E. coli* is introduced with no genes other than:

(a) the gene encoding active acetoacetate decarboxylase of the genus *Clostridium* is a gene encoding active acetoacetate decarboxylase of *Clostridium acetobutylicum;*

(b) the gene encoding active isopropyl alcohol dehydrogenase of the genus *Clostridium* is a gene encoding active isopropyl alcohol dehydrogenase of *Clostridium beijerinckii,*

(c) the gene encoding active CoA transferase of the genus *Escherichia* is a gene encoding active CoA transferase of *Escherichia coli*; and (d) the gene encoding active thiolase of the genus *Escherichia* is a gene encoding active thiolase of *Escherichia coli.*

9. The *E. coli* according to claim 5, wherein the *E. coli* is introduced with no genes other than:

(a) the gene encoding active acetoacetate decarboxylase of the genus *Clostridium* is a gene encoding active acetoacetate decarboxylase of *Clostridium acetobutylicum;*

(b) the gene encoding active isopropyl alcohol dehydrogenase of the genus *Clostridium* is a gene encoding active isopropyl alcohol dehydrogenase of *Clostridium beijerinckii,*

(e) the gene encoding active CoA transferase of the genus *Clostridium* is a gene encoding active CoA transferase of *Clostridium acetobutylicum*; and (f) the gene encoding active thiolase of the genus *Clostridium* is a gene encoding active thiolase of *Clostridium acetobutylicum.*

10. A method for producing isopropyl alcohol, the method comprising producing isopropyl alcohol from a plant-derived material using the isopropyl alcohol-producing bacterium according to claim 1.

11. The method for producing isopropyl alcohol according to claim 10, the method comprising further adding, to a mixture comprising the isopropyl alcohol-producing bacterium and the plant-derived material, a compound containing nitrogen.

12. The method for producing isopropyl alcohol according to claim 10, the method comprising adding, to a mixture comprising the isopropyl alcohol-producing bacterium and the plant-derived material, a nitrogen-containing compound which may produce an ammonium ion in water, such that a content of the nitrogen-containing compound is in a range of from 0.04% to 10.6% (w/w) in terms of % by mass of the total nitrogen atoms, with respect to the total mass of the culture medium in the mixture at the start of culturing.

13. The method for producing isopropyl alcohol according to claim 10, comprising:

culturing the isopropyl alcohol-producing bacterium while supplying a gas to the mixture comprising the isopropyl alcohol-producing bacterium and the plant-derived material: and collecting isopropyl alcohol produced by the culture.

14. The method for producing isopropyl alcohol according to claim 13, wherein the gas comprises oxygen.

15. The method for producing isopropyl alcohol according to claim 13, wherein the amount of the gas supplied is 0.02 vvm to 2.0 vvm.

16. The method for producing isopropyl alcohol according to claim 13, wherein the amount of the gas supplied is 0.1 vvm to 1.5 vvm.

17. The method for producing isopropyl alcohol according to claim 13, wherein the collecting comprises contacting, with a capture liquid which captures isopropyl alcohol, the isopropyl alcohol evaporated from the culture obtained in the culturing.

18. The method for producing isopropyl alcohol according to claim 13, wherein the collecting comprises liquefying the evaporated isopropyl alcohol followed by contacting the liquefied isopropyl alcohol with a capture liquid.

* * * * *